(12) United States Patent
He et al.

(10) Patent No.: US 11,219,645 B2
(45) Date of Patent: Jan. 11, 2022

(54) TUMOR INFILTRATING LYMPHOCYTES FOR TREATMENT OF CANCER

(71) Applicant: Duke University, Durham, NC (US)

(72) Inventors: You-Wen He, Durham, NC (US); Yu Wang, Durham, NC (US)

(73) Assignee: Duke University, Durham, NC (US)

( * ) Notice: Subject to any disclaimer, the term of this patent is extended or adjusted under 35 U.S.C. 154(b) by 255 days.

(21) Appl. No.: 15/777,253

(22) PCT Filed: Nov. 18, 2016

(86) PCT No.: PCT/US2016/062739
§ 371 (c)(1),
(2) Date: May 18, 2018

(87) PCT Pub. No.: WO2017/087784
PCT Pub. Date: May 26, 2017

(65) Prior Publication Data
US 2018/0250338 A1    Sep. 6, 2018

Related U.S. Application Data

(60) Provisional application No. 62/265,511, filed on Dec. 10, 2015, provisional application No. 62/265,513, filed on Dec. 10, 2015, provisional application No. 62/265,508, filed on Dec. 10, 2015, provisional application No. 62/257,143, filed on Nov. 18, 2015.

(51) Int. Cl.
| | |
|---|---|
| *A61K 35/17* | (2015.01) |
| *A61K 45/06* | (2006.01) |
| *C07K 14/705* | (2006.01) |
| *C07K 14/54* | (2006.01) |
| *C07K 16/28* | (2006.01) |
| *A61K 31/555* | (2006.01) |
| *A61K 33/243* | (2019.01) |
| *A61P 35/00* | (2006.01) |
| *A61K 38/00* | (2006.01) |

(52) U.S. Cl.
CPC ............ *A61K 35/17* (2013.01); *A61K 31/555* (2013.01); *A61K 33/243* (2019.01); *A61K 45/06* (2013.01); *A61P 35/00* (2018.01); *C07K 14/54* (2013.01); *C07K 14/5428* (2013.01); *C07K 14/705* (2013.01); *C07K 16/2818* (2013.01); *A61K 38/00* (2013.01); *C07K 2319/33* (2013.01); *C07K 2319/75* (2013.01)

(58) Field of Classification Search
CPC .... A61K 35/17; A61K 45/06; C07K 14/5428; A61P 35/00
See application file for complete search history.

(56) References Cited

U.S. PATENT DOCUMENTS

| | | |
|---|---|---|
| 5,231,012 A | 7/1993 | Mosmann et al. |
| 6,914,128 B1 | 7/2005 | Salfeld et al. |
| 8,404,814 B2 | 3/2013 | Neri et al. |
| 2005/0233451 A1* | 10/2005 | Liu .................... A61K 39/0011 435/372 |
| 2009/0324539 A1 | 12/2009 | Cai et al. |
| 2011/0044983 A1 | 2/2011 | Lambris et al. |
| 2013/0136754 A1 | 5/2013 | Tedder et al. |
| 2014/0105912 A1 | 4/2014 | Noelle |
| 2014/0219999 A1 | 8/2014 | Lambris et al. |
| 2015/0183881 A1 | 7/2015 | Bedi et al. |

FOREIGN PATENT DOCUMENTS

| | | |
|---|---|---|
| WO | 1998/016238 A2 | 4/1998 |
| WO | WO 2001/058956 A2 | 8/2001 |
| WO | WO 2002/002773 A2 | 1/2002 |
| WO | WO 2014/023673 A1 | 2/2014 |
| WO | 20140176373 A2 | 10/2014 |
| WO | WO 2016/210289 A1 | 12/2016 |

OTHER PUBLICATIONS

Emmerich et al. (Cancer Res 72: 3570-3581, May 2012 (Year: 2012).*
Santojemma et al, Cancer Biol Thera, 16:807-820, Jun. 2015 (Year: 2015).*
Foppen et al, Mol Oncol 9:1918-35, 2015, Epub Oct. 30, 2015 (Year: 2015).*
Chan et al, Receptors Clin Investig 2(4), HHS Public access p. 1-15, Epub Nov. 4, 2015 (Year: 2015).*
Emmerich et al (Cancer Res 72: 3570-81, 2012 (Year: 2012).*
Chen et al, J Immunol 147:528-534, 1991 (Year: 1991).*
Downs-Canner et al, Ann Surg Oncol 23:655-662, published online Aug. 2015 (Year: 2015).*
International Search Report and Written Opinion, PCT/US2016/062739 dated Mar. 3, 2017.
OFT, "IL-10: Master Switch from Tumor-Promoting Inflammation to Antitumor Immunity," Cancer Immunology Research, Mar. 1, 2014 (Mar. 1, 2014), vol. 2, pp. 194-199.
Wang, et al., "Autocrine Complement Inhibits IL 10-Dependent T-Cell-Mediated Antitumor Immunity to Promote Tumor Progression," Cancer Discovery, Sep. 1, 2016 (Sep. 1, 2016), vol. 6, pp. 1022-1035.
Ames et al., "Identification of a selective nonpeptide antagonist of the anaphylatoxin C3a receptor that demonstrates antiinflammatory activity in animal models," J Immunol, 2001, 166, 6341-6348.

(Continued)

*Primary Examiner* — Lei Yao
(74) *Attorney, Agent, or Firm* — Michael Best & Friedrich LLP

(57) ABSTRACT

Tumor infiltrating lymphocytes (TILs) are white blood cells that are actively recruited to the tumor site to mount an immune response against tumor growth and metastasis. The disclosure provides methods for treating cancer that comprise steps of isolating CD8+ T cells from a sample derived from a subject, expanding the CD8+ T cells in the presence of interleukin-10, and administering the expanded CD8+ T cells to the subject. Methods of treating cancer may be used in combination with inhibitors of the complement signaling pathway.

9 Claims, 35 Drawing Sheets

Specification includes a Sequence Listing.

(56) References Cited

OTHER PUBLICATIONS

Barbas et al., "In vitro evolution of a neutralizing human antibody to human immunodeficiency virus type 1 to enhance affinity and broaden strain cross-reactivityv," Proc. Nat. Acad. Sci. USA, 1994, 91: 3809-3813.

Berg et al., "Enterocolitis and colon cancer in interleukin-10-deficient mice are associated with aberrant cytokine production and CD4(+) THI-like responses," J Clin Invest, 1996, 98, 1010-1020.

Berman et al., "Systemic administration of cellular IL-10 induces an effective, specific, and long-lived immune response against established tumors in mice," J Immunol, 1996, 157, 231-238.

Bjorge et al., "Ascitic complement system in ovarian cancer," British journal of cancer, 2005, 92, 895-905.

Brahmer et al., "Safety and activity of anti-PD-L1 antibody in patients with advanced cancer," N Engl J Med, 2012, 366, 2455-2465.

Carli et al., "Fluctuation of serum complement levels in children with neuroblastoma," Cancer, 1979, 43, 2399-2404.

Carroll, "The complement system in regulation of adaptive immunity," Nat Immunol, 2004, 5, 981-986.

Chen et al., "Fusion protein linkers: property, design and functionality," Adv Drug Deliv Rev, 2013, 65(10): 1357-1369.

Chen et al., "IL-10: a novel cytotoxic T cell differentiation factor," J Immunol, 1991, 147, 528-534.

Corrales et al., "Anaphylatoxin C5a creates a favorable microenvironment for lung cancer progression," J Immunol, 2012, 189, 4674-4683.

Dong et al., "87-H1, a third member of the B7 family, co-stimulates T-cell proliferation and interleukin-10 secretion," Nat Med, 1999, 5, 1365-1369.

Dunkelberger et al., "C5aR expression in a novel GFP reporter gene knockin mouse: implications for the mechanism of action of C5aR signaling in T cell immunity," J Immunol, 2012, 188, 4032-4042.

Emmerich et al., "IL-10 directly activates and expands tumor-resident CD8(+) T cells without de novo infiltration from secondary lymphoid organs," Cancer Res, 2012, 72, 3570-3581.

Fang et al., "Complement-dependent enhancement of CD8+ T cell immunity to lymphocytic choriomeningitis virus infection in decay-accelerating factor-deficient mice," J Immunol, 2007, 179, 3178-3186.

Flight, "Avoiding bad complement in Alzheimer's disease," Nature reviews, 2009, Neuroscience 8, 316.

Friesen et al., "The C3a receptor antagonist SB 290157 has agonist activity," Immunol Lett, 2005, 100, 139-145.

Fujii et al., "Interleukin-10 promotes the maintenance of antitumor CD8(+) T-cell effector function in situ," Blood, 2001, 98, 2143-2151.

Fust et al., "C1 and C4 abnormalities in chronic lymphocytic leukaemia and their significance," Immunol Lett, 1987, 14, 255-259.

Gerlini et al., "Metastatic melanoma secreted IL-10 down-regulates CD1 molecules on dendritic cells in metastatic tumor lesions," The American journal of pathology, 2004, 165, 1853-1863.

Gminski et al., "Immunoglobulins and complement components levels in patients with lung cancer," Romanian journal of internal medicine = Revue roumaine de medecine interne, 1992, 30, 39-44.

Gottlin et al., "Isolation of novel EGFR-specific VHH domains," Journal of Biomolecular Screening, 2009, 14: 77-85.

Groux et al., "Inhibitory and stimulatory effects of IL-10 on human CD8+ T cells," J Immunol, 1998, 160, 3188-3193.

Gunn et al., "Opposing roles for complement component C5a in tumor progression and the tumor microenvironment," J Immunol, 2012, 189, 2985-2994.

Hattori et al., "Possible contribution of circulating interleukin-10 (IL-10) to anti-tumor immunity and prognosis in patients with unresectable hepatocellular carcinoma," Hepatology research: the official journal of the Japan Society of Hepatology, 2003, 27, 309-314.

Hawkins et al., "Selection of phage antibodies by binding affinity. Mimicking affinity maturation," J. Mol. Biol., 1992, 226: 889-896.

Heeger et al., "Novel roles of complement in T effector cell regulation," Immunobiology, 2012, 217, 216-224.

Hemmerlee et al. "The Antibody-based Targeted Delivery of Interleukin-4 and 12 to the Tumor Neovasculature Eradicates Tumors in Three Mouse Models of Cancer," International Journal of Cancer, Jan. 15, 2014, vol. 134, pp. 467-477.

Holliger et al., "'Diabodies": small bivalent and bispecific antibody fragments," Proc. Natl. Acad. Sci. USA, 1993, 90(14): 6444-6448.

Itakura et al., "IL-10 expression by primary tumor cells correlates with melanoma progression from radial to vertical growth phase and development of metastatic competence," Modem pathology: an official journal of the United States and Canadian Academy of Pathology, Inc., 2011, 24, 801-809.

Jackson et al., "In vitro antibody maturation. Improvement of a high affinity, neutralizing antibody against IL-1 beta," J. Immunol., 1995, 154(7): 3310-3319.

Janelle et al., "Transient complement inhibition promotes a tumor-specific immune response through the implication of natural killer cells," Cancer Immunol Res, 2014, 2, 200-206.

Jovasevic et al., "Importance of IL-10 for CTLA-4-mediated inhibition of tumor-eradicating immunity," J Immunol, 2004, 172, 1449-1454.

Kamanaka et al., "Expression of interleukin-10 in intestinal lymphocytes detected by an interleukin-10 reporter knockin tiger mouse," Immunity, 2006, 25, 941-952.

Kerr, "A novel formaulation of niclosamide treats metastatic osteosarcoma in vivo," 2017.

Kim et al., "Complement C5a receptor is essential for the optimal generation of antiviral CD8+ T cell responses," J Immunol, 2004, 173, 2524-2529.

Kuhn et al., "Interleukin-10-deficient mice develop chronic enterocolitis," Cell, 1993, 75, 263-274.

Kwan et al., "Signaling through C5a receptor and C3a receptor diminishes function of murine natural regulatory T cells," J Exp Med, 2013, 210, 257-268.

Lalli et al., "Locally produced C5a binds to T cell-expressed C5aR to enhance effector T-cell expansion by limiting antigen-induced apoptosis," Blood, 2008, 112, 1759-1766.

Li et al., "TLR4 signaling pathway in mouse Lewis lung cancer cells promotes the expression of TGF-beta 1 and IL-10 and tumor cells migration," Biomedical materials and engineering, 2014, 24, 869-875.

Liszewski et al., "Intracellular complement activation sustains T cell homeostasis and mediates effector differentiation," Immunity, 2013, 39, 1143-1157.

Liu et al., "IFN-gamma and IL-17 production in experimental autoimmune encephalomyelitis depends on local APC-T cell complement production," J Immunol, 2008, 180, 5882-5889.

Maness et al., "Serum complement levels in patients with digestive tract carcinomas and other neoplastic diseases," Oncology, 1977, 34, 87-89.

Marcus et al., "Recognition of tumors by the innate immune system and natural killer cells," Advances in immunology, 2014, 122, 91-128.

Markiewski et al., "Modulation of the antitumor immune response by complement," Nat Immunol, 2008, 9, 1225-1235.

Marks et al., "By-passing immunization: building high affinity human antibodies by chain shuffling," BioTechnology, 1992, 10: 779-783.

Matsutani et al., "Cellular immunity and complement levels in hosts with brain tumours," Neurosurgical review, 1984, 7, 29-35.

Merrifield, "Solid phase synthesis," Science, 1986, 233: 341-347.

Milstein et al., "Hybrid hybridomas and their use in immunohistochemistry," Nature, 1983, 305(5934): 537-540.

Mombaerts et al., "Mutations in T-cell antigen receptor genes alpha and beta block thymocyte development at different stages," Nature, 1992, 360, 225-231.

Mook et al., "Structure-activity studies of Wnt/β-catenin inhibition in the Niclosamide chemotype: Identification of derivatives with improved drug exposure," Bioorganic & Medicinal Chemistry, 2015, 23(17): 5829-5838.

(56) References Cited

OTHER PUBLICATIONS

Mumm et al., "IL-10 elicits IFNgamma-dependent tumor immune surveillance," Cancer Cell, 2011, 20, 781-796.
Nakayama et al., "C3 promotes expansion of CD8+ and CD4+ T cells in a Listeria monocytogenes infection," J Immunol, 2009, 183, 2921-2931.
Neven et al., "A Mendelian predisposition to B-cell lymphoma caused by IL-10R deficiency," Blood, 2013, 122, 3713-3722.
Niehans et al., "Human carcinomas variably express the complement inhibitory proteins CD46 (membrane cofactor protein), CD55 (decay-accelerating factor), and CD59 (protectin)," The American journal of pathology, 1996, 149, 129-142.
Nishikawa et al., "Regulatory T cells in tumor immunity," International journal of cancer. Journal international du cancer, 2010, 127, 759-767.
Nishioka et al., "The complement system in tumor immunity: significance of elevated levels of complement in tumor bearing hosts," Annals of the New York Academy of Sciences, 1976, 276, 303-315.
Nunez-Cruz et al., "Genetic and pharmacologic inhibition of complement impairs endothelial cell function and ablates ovarian cancer neovascularization," Neoplasia, 2012, 14, 994-1004.
Ouyang et al., "Regulation and functions of the IL-10 family of cytokines in inflammation and disease," Annual review of immunology, 2011, 29, 71-109.
Pardoll, "The blockade of immune checkpoints in cancer immunotherapy," Nat Rev Cancer, 2012, 12, 252-264.
Pio et al., "The role of complement in tumor growth," Adv Exp Med Biol, 2014, 772, 229-262.
Reid et al., "A convergent solution-phase synthesis of the macrocycle Ac-Phe-[Orn-Pro-D-Cha-Trp-Arg], a potent new antiinflammatory drug," J Org Chem, 2003, 68, 4464-4471.
Ricklin et al., "Complement: a key system for immune surveillance and homeostasis," Nat Immunol, 2010, 11, 785-797.
Roers et al., "Interferon-dependent IL-10 production by Tregs limits tumor Th17 inflammation," J Clin Invest, 2013, 123, 4859-4874.
Rosenberg, "IL-2: the first effective immunotherapy for human cancer," Journal of immunology, 2014, 192, 5451-5458.
Roszkowski et al., "Simultaneous generation of CD8+ and CD4+ melanoma-reactive T cells by retroviral-mediated transfer of a single T-cell receptor," Cancer Res., 2005, 65(4): 1570-1576.
Roychoudhuri et al., "BACH2 represses effector programs to stabilize T(reg)-mediated immune homeostasis," Nature, 2013, 498, 506-510.
Ruffell et al., "Macrophage IL-10 blocks CD8+ T celldependent responses to chemotherapy by suppressing IL-12 expression in intratumoral dendritic cells," Cancer Cell, 2014, 26, 623-637.
Santin et al., "Interleukin-10 increases Th1 cytokine production and cytotoxic potential in human papillomavirus-specific CD8(+) cytotoxic T lymphocytes," J Viral, 2000, 74, 4729-4737.
Schier et al., "Identification of functional and structural amino-acid residues by parsimonious mutagenesis," Gene, 1995, 169: 147-155.
Schug, "Using TESS to predict transcription factor binding sites in DNA sequence," Curr Protoc Bioinformatics, 2008, Chapter 2, Unit 2 6.
Schwarz et al., "Stimulation of cytolytic activity by interleukin-10," Journal of immunotherapy with emphasis on tumor immunology: official journal of the Society for Biological Therapy, 1994, 16, 95-104.
Sharma et al., "Immune checkpoint targeting in cancer therapy: toward combination strategies with curative potential," Cell, 2015, 161, 205-214.
Staerz et al., "Hybrid antibodies can target sites for attack by T cells," Nature, 1985, 314(6012): 628-631.
Strainic et al., "Absence of signaling into CD4(+) cells via C3aR and C5aR enables autoinductive TGF-beta1 signaling and induction of Foxp3(+) regulatory T cells," Nat Immunol, 2013, 14, 162-171.
Strainic et al., "Locally produced complement fragments C5a and C3a provide both costimulatory and survival signals to naive CD4+ T cells," Immunity, 2008, 28, 425-435.
Sung et al., "IL-10 promotes tumor aggressiveness via upregulation of CIP2A transcription in lung adenocarcinoma," Clin Cancer Res, 2013, 19, 4092-4103.
Suresh et al., "Complement component 3 is required for optimal expansion of CD8 T cells during a systemic viral infection," J Immunol, 2003, 170, 788-794.
Tanikawa et al., "Interleukin-10 ablation promotes tumor development, growth, and metastasis," Cancer Res, 2012, 72, 420-429.
Topalian et al., "Safety, activity, and immune correlates of anti-PD-1 antibody in cancer," N Engl J Med, 2012, 366, 2443-2454.
Trandem et al., "Highly activated cytotoxic CD8 T cells express protective IL-10 at the peak of coronavirus-induced encephalitis," J Immunol, 2011, 186, 3642-3652.
Tsukumo et al., "Bach2 maintains T cells in a naive state by suppressing effector memory-related genes," Proc Natl Acad Sci USA, 2013, 110, 10735-10740.
Vadrevu et al., "Complement c5a receptor facilitates cancer metastasis by altering T-cell responses in the metastatic niche," Cancer Res, 2014, 74, 3454-3465.
Vahedi et al., "Super-enhancers delineate diseaseassociated regulatory nodes in T cells," Nature, 2015, 520, 558-562.
van der Touw et al., "Cutting edge: Receptors for C3a and C5a modulate stability of alloantigen-reactive induced regulatory T cells," J Immunol, 2013, 190, 5921-5925.
Wang et al., "IL-10 enhances CTLmediated tumor rejection by inhibiting highly suppressive CD4 T cells and promoting CTL persistence in a murine model of plasmacytoma," Oncoimmunology, 2015, 4, el 014232.
Wessels et al., "Studies of group B streptococcal infection in mice deficient in complement component C3 or C4 demonstrate an essential role for complement in both innate and acquired immunity," Proc Natl Acad Sci USA, 1995, 92, 11490-11494.
Wu et al., "Simultaneous targeting of multiple disease mediators by a dual-variable-domain immunoglobulin," Nature Biotechnology, 2007, 25(11): 1290-1297.
Yang et al., "In vitro priming of tumorreactive cytolytic T lymphocytes by combining IL-10 with B7-CD28 costimulation," J Immunol, 1995, 155, 3897-3903.
Yelton et al., "Affinity maturation of the BR96 anti-carcinoma antibody by codon-based mutagenesis," J. Immunol., 1995, 155: 1994-2004.
Ytting et al., "Increased activity of the mannan-binding lectin complement activation pathway in patients with colorectal cancer," Scandinavian journal of gastroenterology, 2004, 39, 674-679.
Ytting et al., "Serum mannanbinding lectin-associated serine protease 2 levels in colorectal cancer: relation to recurrence and mortality," Clin Cancer Res, 2005, 11, 1441-1446.
International Search Report and Written Opinion for Application No. PCT/US2016/062717 dated Mar. 3, 2017 (13 pages).
Mannino, PubMed; DOI: 10.1016/j.canlet.2015.07.009; Cancer Letters 367(2), Jul. 2015.
Zhao, et al. Serum IL-10 Predicts Worse Outcome in Cancer Patients: A Meta-Analysis, PLOS ONE; DOI:10.1371/1371/journal. pone.0139598; Oct. 6, 2015.
Chinese Patent Office Action for Application No. 201680078606.4 dated Aug. 11, 2021 (11 pages, English translation included).

\* cited by examiner

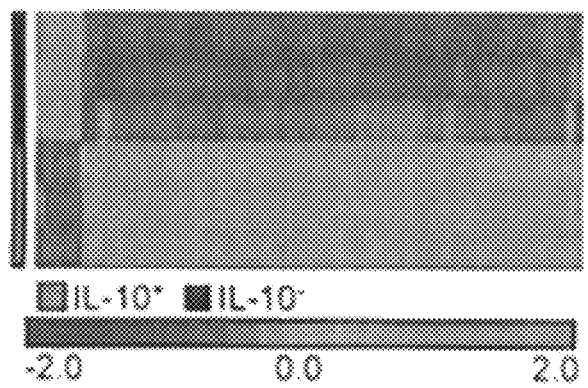

FIG. 1A

```
     Pathway
1  ─────────── Immune response_Alternative complement pathway
2  ─────────── Immune response_IL-18 signaling
3  ─────────── Immune response_Classical complement pathway
4  ─────────── Immune response_HSP60 and HSP70 TLR signaling pathway
5  ─────────── Immune response_Lectin induced complement pathway
6  ─────────── Immune response_CCL2 signaling
7  ─────────── Immune response_ETV3 affect on CSF1-promoted macrophage differentiation
8  ─────────── Immune response_IL-5 signaling
9  ─────────── Development_Transcription regulation of granulocyte development
10 ─────────── Immune response_MIF-induced cell adhesion, migration and angiogenesis
```

FIG. 1B

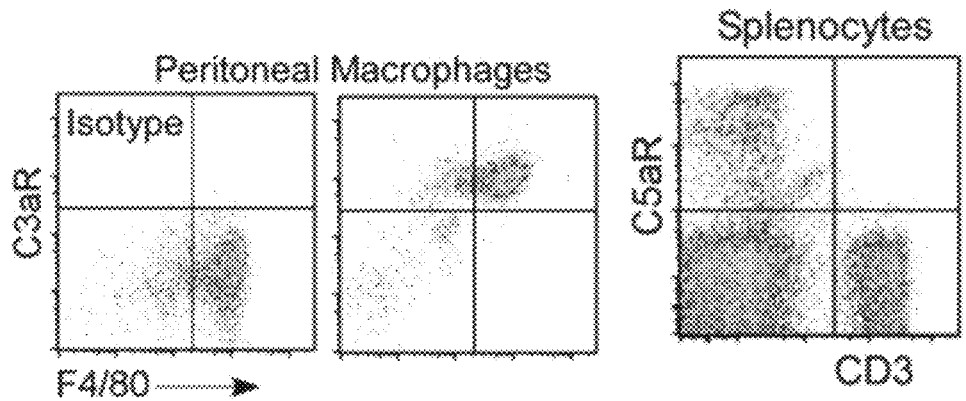
FIG. 11A  FIG. 11B
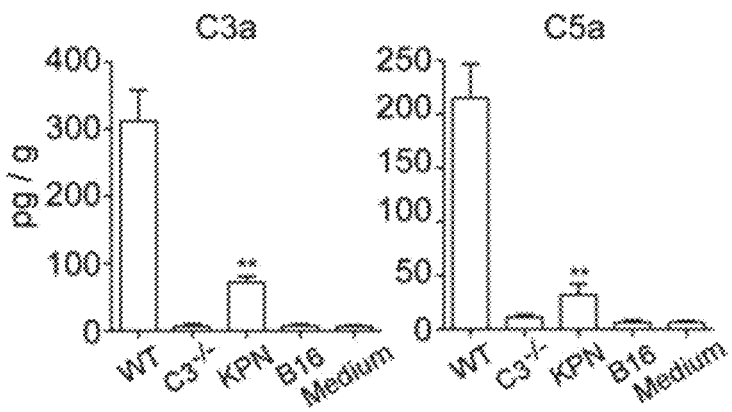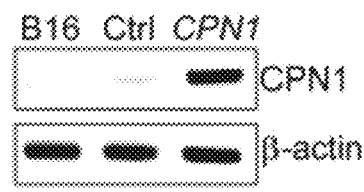
FIG. 11C  FIG. 11D

TUMOR INFILTRATING LYMPHOCYTES FOR TREATMENT OF CANCER

CROSS-REFERENCE TO RELATED APPLICATIONS

This application is a national stage filing under 35 U.S.C. 371 of International Patent Application No. PCT/US2016/062739, filed Nov. 18, 2016, which application claims priority to U.S. Provisional Patent Application No. 62/257,143, filed on Nov. 18, 2015, and to U.S. Provisional Patent Application Nos. 62/265,508, 62/265,511, and 62/265,513 filed on Dec. 10, 2015, the contents of each of which are hereby incorporated by reference in their entireties.

STATEMENT OF GOVERNMENT INTEREST

This invention was made with U.S. Government support under grant number R01 AI074944-01 awarded by the National Institutes of Health. The U.S. Government has certain rights in this invention.

SEQUENCE LISTING

The instant application includes a Sequence Listing which has been submitted electronically in ASCII format and is hereby incorporated by reference in its entirety. Said ASCII copy, created on Sep. 2, 2020, is named 028193-9224-US01_As_Filed_Sequence_Listing.txt and is 4,111 bytes in size.

TECHNICAL FIELD

The present disclosure relates to tumor infiltrating lymphocytes and compositions and methods for use in treating cancer.

BACKGROUND

Tumor infiltrating lymphocytes (TILs) are white blood cells that are actively recruited to the tumor site to mount an immune response against tumor growth and metastasis. A variety of signaling pathways control the activation of TILs, and many have been investigated as targets for cancer therapies. However, current therapies focusing on activating TILs are only effective for a small percentage of patients, highlighting a need for improved therapeutic approaches for treating cancer.

SUMMARY

In an aspect, the disclosure provides methods for treating a cancer in a subject in need thereof, comprising isolating CD8+ T cells from a sample derived from a subject, exposing the CD8+ T cells to interleukin-10, exposing the CD8+ T cells to interleukin-2, expanding the CD8+ T cells, and administering the expanded CD8+ T cells to the subject. In some embodiments, the CD8+ T cells may be exposed to interleukin-2 prior to being exposed to interleukin-10. In other embodiments, the CD8+ T cells may be exposed to interleukin-2 and interleukin-10 simultaneously. In some embodiments, the disclosed methods may further comprise administering to the subject a therapeutically effective amount of a complement inhibitor.

BRIEF DESCRIPTION OF THE DRAWINGS

FIG. 1 shows regulation of IL-10 expression in CD8+ T cells by complement. FIG. 1A shows a heat map of the differentially expressed genes in IL-10+ and IL-10–CD8+ T cells. FIG. 1B shows pathway analysis of differentially expressed genes as shown in FIG. 1A.

FIG. 2 shows suppression of T-cell—mediated antitumor immunity by complement.

FIG. 3 shows non-CD8+ T-cell responses in tumor-bearing mice. B16F10 melanoma cells (2×10$^5$/mouse) were subcutaneously inoculated into wild-type (WT) and C3−/− mice. The draining lymph nodes (dLNs) and tumors were treated with collagenase and DNase to generate a single-cell suspension. Leukocytes were pregated on CD45+ cells.

FIG. 4 shows an essential role for IL-10 in the antitumor response in C3−/− mice.

FIG. 5 shows that IL-10 enhances the function of TILs from patients with cancer.

FIG. 6 shows suppression of IL-10 production by autocrine C3.

FIG. 9 shows non-CD8+ T cell responses in tumor bearing mice. B16F10 melanoma cells (2×10$^5$/mouse) were subcutaneously inoculated into WT and C3−/− mice. The draining lymph nodes and tumors were dissected and treated with collagenase and DNase to obtain single cell suspensions. Leukocytes were pre-gated on CD45 positive cells.

FIG. 12 shows the transcriptional repression of IL-10 by Bach2. FIG. 12E shows Il10 mRNA level in Bach2-expressing CD8+ T cells. Bach2-expressing and control CD8+ T cells shown in FIG. 12D were sorted by flow cytometry and determined by real-time RT-PCR for IL-10 mRNA expression. Data were normalized to 18s rRNA. FIG. 12C-E show representative of three repeats. Error bar indicates SEM. **p≤0.01.

DETAILED DESCRIPTION

Figure 1C:
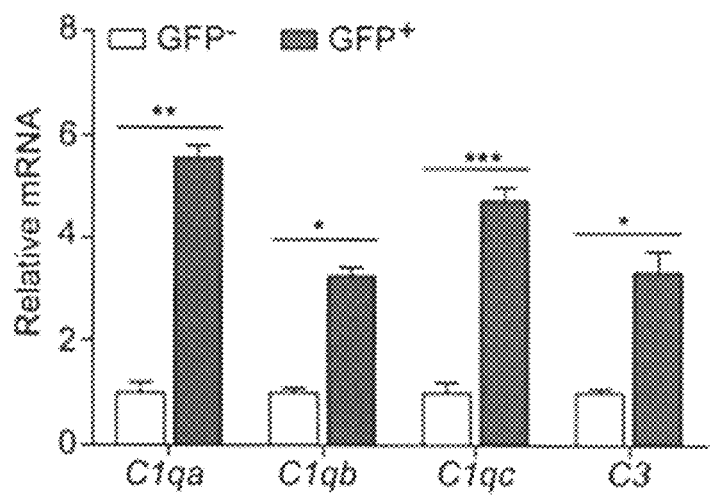
FIG. 1C and FIG. 1D shows mRNA expression of complement (FIG. 1C) and complement receptors (FIG. 1D) in IL-10+CD8+ (GFP+) and IL-10CD8+ (GFP−) T cells. Plots show relative expression levels of mRNAs for each indicated gene based on gene chip data. Shown are the mean±SEM from data deposited by Trandem and colleagues (*Journal of Immunology*, 186:3642-52.)

The present disclosure is directed to compositions and methods for treating cancer. Tumor-infiltrating lymphocytes (TILs) are mononuclear immune cells that are recruited to a tumor site and are implicated in killing tumor cells. TILs comprise a mix of different types of cells, including T cells, B cells, natural killer (NK) cells, and macrophages, with T cells being the most abundant cell type.

Interleukin10 (IL-10) is largely considered an immune inhibitory cytokine as it inhibits the activation of many different cell types including CD4+ T cells, dendritic cells, and macrophages. In contrast to its inhibitory effects on many types of cells, IL-10 activates CD8+ TILs and enhances their antitumor activity. However, CD8+ TILs do not express IL-10 under normal conditions. As such, there is a need for cancer therapies that activate IL-10 to enhance CD8+ TIL antitumor activity.

The disclosure further provides methods for treating cancer that comprise steps of isolating CD8+ T cells from a sample derived from a subject, expanding the CD8+ T cells in the presence of interleukin-10, and administering the expanded CD8+ T cells to the subject.

Complement signaling exhibits multifactorial inhibition of antitumor immunity. Complement inhibits IL-10 production in CD8+ TILs, reducing their antitumor activity. Complement also recruits immunosuppressive myeloid-derived suppressor cells (MDSCs) and prevents activation of natural killer (NK) cells in various tumor models. In another aspect, the disclosure describes methods of activating CD8+ TILs by inhibiting complement signaling. Some embodiments may include methods of treating cancer that comprise administering CD8+ T cells expanded ex vivo in the presence of interleukin-10 and inhibiting complement signaling.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of disclosed embodiments. All publications, patent applications, patents, and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "administration" or "administering," as used herein refers to providing, contacting, and/or delivery by any appropriate route to achieve the desired effect. The disclosed compositions may be administered to a subject in numerous ways familiar to those of ordinary skill in the art, including, for example, local administration or systemic administration, which can be achieved by, for example, oral administration, subcutaneous injection, intravenous injection, topical administration, or implant.

"Affinity Matured Antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, multispecific antibodies, human antibodies, humanized antibodies (fully or partially humanized), antibodies derived from an animal such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.). "Antibody" and "antibodies" further include recombinant antibodies, monoclonal antibodies, affinity matured antibodies, bispecific antibodies, dual specific antibodies, antibody derivatives, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., Journal of Biomolecular Screening, 14:77-85 (2009)) and VNAR fragments, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007)) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site.

Immunoglobulin molecules can be of any type (for example, IgG, IgE, IgM, IgD, IgA, and IgY), class (for example, IgG1, IgG2, IgG3, IgG4, IgA1, and IgA2), or subclass. The terms "antibody" and "antibodies" also include any antibody fragment, which as used herein refers to a portion of an intact antibody comprising the antigen-binding site or variable region. The portion need not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, single-chain polypeptides containing the three CDRs of the heavy chain variable region, and VHH.

As used herein, the term "anticancer molecule" refers to any molecule that is effective at treating cancer in a subject. In some embodiments, the anticancer molecule comprises an antibody. Suitable anticancer molecules include, but are not limited to, anti-PD-L1 (e.g., BMS-936559, MPDL3280A, and the like), anti-CD40 (e.g., CP-870,893 and the like), anti-TIM3, anti-CTLA4 (e.g., ipilimumab, tremelimumab and the like), anti-PD-1 (e.g., MK-3475, nivolumab and the like), anti-4-1BB (anti-CD137) (e.g., BMS663513, PF-05082566 and the like), anti-CD94 (e.g., IPH2201, and the like), anti-LAG3 (e.g., IMP321, LAG525, BMS-986016, and the like), anti-CD134 (e.g., MED16469 and the like), anti-CD70 (e.g., ARGX-110 and the like), anti-CD27 (e.g., Varlilumab and the like), anti-glucocorticoid-induced TNF receptor (GITR) (e.g., TRX-518, MK-4166 and the like), anti-CD278,anto-GARP (e.g., ARGX-115 and the like), anti-V-domain immunoglobulin suppressor of T-cell activation (VISTA) and combinations thereof. In some embodiments, the anticancer molecule comprises an aptamer.

An "aptamer" herein refers to oligonucleic acid or peptide molecules that are capable of specific, non-covalent binding to its target. Aptamers may comprise a peptide, DNA or RNA sequence. Aptamers may target PD-L1, CD40, TIM3, CTLA4, PD-1, 4-1BB (CD137), CD94, LAG3, CD134, CD70, CD27, glucocorticoid-induced TNF receptor (GITR), CD278, GARP, V-domain immunoglobulin suppressor of T-cell activation (VISTA) and combinations thereof. The binding of an aptamer to its target may result in a change in activity of the target. The binding of an aptamer to its target may inhibit activity of the target. The binding of an aptamer to its target may enhance the activity of the target.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"Cancer" or "tumor" as used interchangeably herein refers to the uncontrolled and unregulated growth of abnormal cells in the body. Cancer may invade nearby parts of the body and may also spread to more distant parts of the body through the lymphatic system or bloodstream. "Cancer cell" or "tumor cell" as used interchangeably herein refers to a cell that divides and reproduces abnormally with uncontrolled growth. A cancer cell can break away and travel to other parts of the body and set up another site, referred to as metastasis. Cancer cells or cancerous cells are also called malignant cells. A cancer cell or cancer cell line may originate from a cancer. For examples, a cancer cell line may be A549 cell line ("A549"), which is a human lung adenocarcinoma epithelial cell line.

Cancers may include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metastatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Complement inhibitor" as used herein refers to a moiety capable of inhibiting complement signaling. Suitable complement inhibitors include, but are not limited to, C5a inhibitors, C5aR inhibitors, C3 inhibitors, C3aR inhibitors, factor D inhibitors, factor B inhibitors, C4 inhibitors, C1q inhibitors, or any combination thereof.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g. a protein domain, said protein domain being linked by covalent or non-covalent bonds. The linkage can be achieved using recombinant nucleic acid techniques according to methods known in the art. The additional domain present in the fusion protein comprising the antibody may be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g. a cytokine or growth hormone), a chemical agent, a peptide, a protein, or a drug, for example.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" or "DVD" as used interchangeably herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig". Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

In an embodiment, a DVD-Ig binding protein not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

The term "effective dosage", "effective amount", or "therapeutically effective amount" as used interchangeably herein means an amount effective for periods of time necessary, to achieve the desired therapeutic result. An effective amount may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of the estrogen receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the disclosed fusion proteins may be administered at various times during the course of treatment of the subject. The times of administration and dosages used will depend on several factors, such as the goal of treatment (e.g., treating v. preventing), condition of the subject, etc. and can be readily determined by one skilled in the art.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"F(ab')2 fragment" as used herein refers to antibodies generated by pepsin digestion of whole IgG antibodies to remove most of the Fc region while leaving intact some of the hinge region. F(ab')2 fragments have two antigen-binding F(ab) portions linked together by disulfide bonds, and therefore are divalent with a molecular weight of about 110 kDa. Divalent antibody fragments (F(ab')2 fragments) are smaller than whole IgG molecules and enable a better penetration into tissue thus facilitating better antigen recognition in immunohistochemistry. The use of F(ab')2 fragments also avoids unspecific binding to Fc receptor on live cells or to Protein A/G. F(ab')2 fragments can both bind and precipitate antigens.

As used herein, the term "ex vivo" refers to a condition applied to a cell, a tissue, or other sample obtained from an organism that takes place outside of the organism. For example, an ex vivo treatment of CD8+ T cells can include exposing CD8+ T cells isolated from a sample obtained from a subject to IL-2 and/or IL-10 in an artificial environment outside the subject. Following an ex vivo treatment, the cell, tissue, or other sample may be administered to the subject or to one or more other subjects.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer rotocol://imgt.cines.fr/texts/IMGTrepertoire/LocusGenes/).

"Functional antigen binding site" as used herein may mean a site on a binding protein (e.g. an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"Fusion protein," or "chimeric protein," as used interchangeably herein refer to a protein comprising polypeptide sequences originally derived from two or more separate proteins.

"Humanized antibody" is used herein to describe an antibody that comprises heavy and light chain variable region sequences from a non-human species (e.g. a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementarity determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1 hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, IgY, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Lung cancer" as used herein refers to cancer that originates in the lung. For example, lung cancer may be cancer of the lung, such as small-cell lung cancer, also known as small-cell lung carcinoma and oat cell cancer, non-small-cell lung carcinoma ("NSCLC"), glandular tumors, carcinoid tumors and undifferentiated carcinomas.

"Non-small-cell lung carcinoma" or "NSCLC" as used interchangeably herein refers to any type of epithelial lung cancer other than small cell lung carcinoma. The three main subtypes of NSCLC are adenocarcinoma, including bronchioloalveolar carcinoma, squamous-cell lung carcinoma, and large-cell lung carcinoma. NSCLCs are relatively insensitive to chemotherapy.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological properties.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Sample," "test sample," "specimen," "sample from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retains at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. "Variant" also can be used to describe a polypeptide or a fragment thereof that has been differentially processed, such as by proteolysis, phosphorylation, or other post-translational modification, yet retains its antigen reactivity.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Complement Inhibition

Complement receptors are expressed on T lymphocytes, and the complement system is a major component in innate and adaptive immunity. As such, complement has long been assumed to play an active role in tumor immune surveillance. However, complement signaling also inhibits antitumor immunity in humans. Complement levels in patients' plasma or tumors positively correlate with tumor size and poor outcome in lung cancer, colorectal cancer, neuroblastoma in children, ovarian cancer, carcinomas of the digestive tract, brain tumors, and chronic lymphocytic leukemia. Complement C3 inhibits IL-10 production in CD8+ TILs through complement receptors C3aR and C5aR.

Complement deficient mice are resistant to tumor development in a T cell- and IL-10-dependent manner. CD8+ TILs from complement-deficient mice express IL-10 and exhibit enhanced effector function. Mice lacking complement components (C3,C4, or C5aR) or treated with complement inhibitors exhibit tumor resistance or suppressed metastasis. Complement may also inhibit antitumor immunity by recruiting MDSCs or by inhibiting NK-cell activation.

Another aspect of the present disclosure provides a method of treating a cancer in a subject comprising administering to the subject a therapeutically effective amount of one or more complement inhibitors. In some aspects, inhibition of complement signaling may be used to enhance the efficacy of another cancer treatment. For example, human anti-PD-1 antibodies may be used to treat melanoma and lung cancer. However, only about 10-30% of patients respond to treatment with anti-PD-1. Complement signaling-mediated immune suppression does not affect PD1 on T cells or PD-L1 on tumors, suggesting complement signaling and PD-1 signaling are two independent pathways. Combined blockade of complement signaling by antagonists to C3aR and C5aR and anti-PD-1 may enhance the efficacy of anti-PD-1 treatment.

In certain embodiments, the complement inhibitor may comprise one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof. Suitable complement inhibitors may include, but are not limited to, SB-290157 (a non-peptide small compound developed as a selective antagonist of C3aR), PMX205 (the cyclic hexapeptide hydrocinnamate-(L-ornithine-proline-D-cyclohexlalanine-tryptophan-arginine) is a well-defined C5aR antagonist), Factor D inhibitors (e.g., BCX1470 and the like), sCR1-sLe$^x$/TP-20, Mirococept, TNX-234, TNX-558, TA106, Neutrazumab, anti-properdin, HuMax-CD38, ARC1905, JPE-1375, JSM-7717, C1INH, Rhucin/rhC11NH, sCR1/TP10, CAB-2/MLN-2222, Eculizumab, Pexelizumab, Ofatumumab, Compstatin/POT-4, PMX-53, rhMBL and the like and combinations thereof 3. Interleukin-10

IL-10 is a cytokine with multiple, pleotropic effects in immunoregulation and inflammation. IL-10 has immunosuppressive effects, including inhibition of pro-inflammatory cytokines such as TNFα, IL-1(3, IL-2, IL-3, IL-12, and IFNγ, suppression of antigen presentation, and suppression of CD4+ T cell activation. IL-10 promotes tumor growth and progression in various tumor models. Despite its inhibitory effects on many types of cells, IL-10 serves to activate and expand CD8+ tumor-infiltrating lymphocytes (TILs) and promote their antitumor activity.

In some embodiments, interleukin-10 may comprise an interleukin-10 protein or a variant thereof. A variant of an interleukin-10 protein may include a peptide or polypeptide that differs in amino acid sequence by the insertion, deletion, or substitution of amino acids, that retains at least one biological activity of IL-10. IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants may be variants not found in nature, although others may be post-translational variants, e.g., glycosylated variants. Any variant of IL-10 can be used provided it retains a suitable level of IL-10 activity. It will be appreciated by those skilled in the art that the forms of IL-10 can vary. For example, one form may comprise a wild-type human IL-10. Alternatively, other modified forms of IL-10 that may have desirable affinity to IL-10R n CD8+ T cells can also be selected.IL-10 can be derived from a mammal, e.g. human or mouse. Human IL-10 (hIL-10) is preferred for treatment of humans in need of IL-10 treatment.

IL-10 can be obtained in a number of ways using standard techniques known in the art, e.g., isolated and purified from culture media of activated cells capable of secreting the protein (e.g., T-cells), chemically synthesized, or recombinant techniques, (see, e.g., Merrifield, Science 233:341-47 (1986); Atherton et al., *Solid Phase Peptide Synthesis, A Practical Approach,* 1989, I.R.L. Press, Oxford; U.S. Pat. No. 5,231,012 which teaches methods for the production of proteins having IL-10 activity, including recombinant and other synthetic techniques). Recombinant human IL-10 is also commercially available, e.g., from PeproTech, Inc., Rocky Hill, N.J.

4. Use of IL-10 in the Expansion of TILs for Adoptive Cell Therapy

Another feature of the present disclosure provides the use of IL-10 in the expansion of TILs for adoptive cell therapy. Adoptive cell therapy (ACT), which describes the transfer of immune cells into a patient, has shown durable clinical efficacy in multiple types of cancer. However, ACT only benefits a small fraction of cancer patients. The efficacy of transferred cells under current clinical ACT protocols is often limited by inefficient engraftment, poor persistence, and weak capability to attack tumor cells.

Although ACT using TCR- and CAR-T-gene engineered T cells has demonstrated some capability of inducing curative responses in patients with advanced cancers, many major issues including inefficient engraftment, poor persistence and weak CTL activity limit existing ACT techniques. Preconditioning of T cells with cytokines may be used to program gene-engineered and antitumor specific T cells into antitumor T cells for ACT, but reliable and efficient conditioning methodology that has a durable impact in vivo remains to be fully established. For example, conditioning of gene-engineered T cells with IL-12 plus IL-2 leads to increased potency but decreased number of the ACT product and IL-15 plus IL-2 results in short-lived CD8+ TILs from human breast cancer. As such, a need exists for optimal conditions that can generate sufficient number of potent antitumor cells ex vivo and exist long-term in vivo after transfer.

IL-10 is an excellent candidate for conditioning of gene engineered T cells for ACT. IL-10 plus IL-2 dramatically enhances both the number and potency of human CD8+ TILs. Given that C3aR/C5aR1 antagonists induce IL-10 production in CD8+ T cells as well as endogenous IL-12 production in macrophages, complement inhibitors may also be used in some embodiments to assist in conditioning CD8+ T cells.

In some aspects, the disclosure provides a method for treating a cancer in a subject in need thereof, the method comprising: isolating CD8+ T cells from a sample derived from a subject, exposing the CD8+ T cells to interleukin-10, exposing the CD8+ T cells to interleukin-2, expanding the CD8+ T cells, and administering the expanded CD8+ T cells to the subject. Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, or serum. In some embodiments, the sample may comprise a tissue sample. In some embodiments, the tissue sample may comprise a tumor sample. In some embodiments, the sample may be a blood sample.

In some embodiments, the CD8+ T cells may be exposed to interleukin-2 prior to being exposed to interleukin-10. In other embodiments, the CD8+ T cells may be exposed to interleukin-2 and interleukin-10 simultaneously. In certain embodiments, the CD8+ T cells may be exposed to interleukin-2, interleukin-10, or interleukin-2 and interleukin-10 for about 1 hour to about four weeks, about 1 hour to about three weeks, about 6 hours to about two weeks, or about 12 hours to about two weeks. In some embodiments, CD8+ T cells may be exposed to interleukin-2, interleukin-10, or interleukin-2 and interleukin-10 for about 1 hour, about 6 hours, about 12 hours, about 24 hours, about 36 hours, about 48 hours, about 3 days, about 5 days, about 1 week, about 10 days, about 2 weeks, about 3 weeks, or about 4 weeks.

Cells may be expanded to and used in any suitable numbers, as would be apparent to a person of ordinary skill in the art. For example, in some embodiments, the CD8+ T cells may be expanded to a density of at least $1 \times 10^6$ cells prior to administration to the subject. In some embodiments, the CD8+ T cells may be expanded to a density of at least $2 \times 10^7$ cells prior to administration to the subject.

The cells can be exposed to interleukin-2 and interleukin-10 in any suitable concentrations, as would be apparent to one skilled in the art. For example, in some embodiments, CD8+ T cells may be exposed to about 10-10,000 U/mL IL-2. In some embodiments, CD8+ T cells may be exposed to about 10-6,000 U/mL IL-2. In some embodiments, CD8+ T cells may be exposed to about 10, about 100, about 120, about 500, about 1,000, about 2,000, about 3,000, about 4,000, about 5,000, about 6,000, about 7,000, about 8,000, about 9,000, or about 10,000 U/mL IL-2. In some embodiments, the concentration of IL-2 may be increased or decreased over time. As a non-limiting example, CD8+ T cells may be exposed to about 10-120 U/mL IL-2 during a first week, followed by increasing the IL-2 concentration to 6,000 IU/mL during a second week. In some embodiments, CD8+ T cells may be exposed to about 1-10,000 U/mL IL-10. In some embodiments, cells may be exposed to about 10-1,000 U/mL IL-10. In some embodiments, cells may be exposed to about 10, about 50, about 100, about 500, about 1,000, about 2,000, about 3,000, about 4,000, about 5,000, about 6,000, about 7,000, about 8,000, about 9,000, or about 10,000 U/mL IL-10. In some embodiments, the concentration of IL-10 may be increased or decreased over time.

In some embodiments, the cells may be exposed ex vivo to a complement inhibitor in addition to interleukin-2 and interleukin-10. The cells can be exposed to a complement inhibitor in any suitable concentration, as would be apparent to one skilled in the art. Cells may be exposed to a complement inhibitor concurrently with IL-2, IL-10, or IL-2 and IL-10, or in some embodiments the cells may be exposed to a complement inhibitor before or after being exposed to IL-2, IL-10, or IL-2 and IL-10.

The disclosed methods may further be used in combination with other known cancer therapies. In some embodiments, the method may further comprise administering to the subject an anti-cancer agent. In some embodiments, the anti-cancer agent may comprise at least one of cisplatin, oxaliplatin, a kinase inhibitor, trastuzumab, cetuximab, panitumumab, lambrolizumab and nivolumab.

In some embodiments, the disclosed methods may further comprise administering a complement inhibitor to the subject. In some embodiments, a complement inhibitor and the expanded CD8+ T cells may be co-administered. In other embodiments, a complement inhibitor may be administered prior to administration of the expanded CD8+ T cells. In other embodiments, the expanded CD8+ T cells may be administered prior to administration of a complement inhibitor.

It is understood that the foregoing detailed description and accompanying examples are merely illustrative and are not to be taken as limitations upon the scope of the disclosure or the claimed subject matter, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use may be made without departing from the spirit and scope thereof.

5. EXAMPLES

Example 1

Methods

Mice and Murine Cell Lines: C57BL/6J (wild-type) mice (stock number: 000664), C3-1–mice (N7, Stock No: 003641), TCRa-1–mice (N13, Stock No: 002116), Il10−/− mice (N13, Stock No: 002251), and Il10 GFP reporter (Tiger) mice (N10, stock number: 008379) were purchased from The Jackson Laboratory. C3−/− mice were further backcrossed to C57BL/6J for 5 generations (N12). N indicates the number of backcrossed generations. Six-to-8-week-old mice were used for all experiments. All mouse strains are of the C57BL/6 genetic background. Mice were housed in a specific pathogen-free facility in the Duke University Medical Center and used according to protocols approved by the Duke University Institutional Animal Care and Use Committee. The B16-F10 murine melanoma cell line was purchased from the ATCC in 2011. E0771, a murine mammary adenocarcinoma, was a gift from Dr. Scott A. Gerber (University of Rochester) in 2013.

Tumor Models: A total of $5\times10^4$ to $4\times10^5$ Bl6F10 or $1\times10^6$ E0771 tumor cells in 100 μL PBS were s.c. inoculated into 6-to-8-week-old mice. Tumor development was monitored daily or every other day. The mice were sacrificed when their tumor volumes reached 2,000 $mm^3$.

Mouse Ex Vivo and In Vitro Experiments: Tumors were cut into small (<3 mm) pieces and incubated in 5 mL dissociation solution [RPMI medium supplemented with Collagenase type I (200 U/mL) and DNase I (100 μg/mL)] for 30 minutes at 37° C. Samples were mixed by pipetting and vortexing every 10 minutes during the incubation. Collagenase (C0130) and DNase I (ND25) were purchased from Sigma-Aldrich. CD45 was used to distinguish tumor infiltrating leukocytes from other cells, and different antibodies targeting surface markers were used for flow cytometry analysis. For intracellular cytokine staining, cells were cultured in complete RPMI for 4 to 6 hours with phorbol 12-myristate 13-acetate, ionomycin, and Brefeldin A (Cell Activation Cocktail; BioLegend).

Microarray Data Analysis: TILs from human lung tumors were in vitro—expanded for 20 days with 6,000 U/mL rIL2 and/or 100 U/mL rIL10. The expanded TILs were activated by incubation in 3 μg/mL anti-CD3/CD28 antibodies for 6 hours. The CD8+ TILs were enriched by negative selection using a kit (Stemcell Technologies). RNA was extracted using TRIzol reagent (Life Technologies) according to the instructions. Microarray analyses were performed using human U133A 2.0 arrays by the Duke University microarray facility. Raw intensities from the CEL files were analyzed using PartekGenomics Suite (Partek Incorporated) with standard background correction to generate an RMA (robust multiarray average intensity) on a log 2 scale for each probe set. Probe sets were filtered for "present" detection in two or more arrays, and the interquartile intensity range was >0.5. The filtered RMA intensities were then analyzed for differential expression using the advanced ANOVA, and differentially expressed genes were generated with/without FDR-adjusted P values using the Benjamini-Hochberg method.

RT-PCR: RNA was isolated with Direct-Zol (Zymo Research) according to the manufacturer's protocol. Complementary DNA was synthesized with SuperScript III Reverse Transcriptase (Life Technologies). Quantitative real-time PCR was performed using a SYBR green—based assay (Applied Biosystems). For mRNA expression in tumor cells, β-actin mRNA was used for normalization across samples.

Complement Receptor Antagonists and PD-1 Antibody Treatment: C3a receptor antagonist SB 290157 was purchased from EMD Millipore, and C5a receptor antagonist PMX205 was purchased from Selleck Chemicals LLC. For E0771 breast tumors, mice were treated intraperitoneally with SB 290157 at 10 mg/kg and PMX205 at 1 mg/kg (both in 5% DMSO/5% ethanol/90% PBS) twice a day from day 9 after tumor implantation. Control mice were treated with 5% DMSO/5%, ethanol/90% PBS. For B16 melanoma, mice were i.p. injected with anti-PD-1 antibody (Clone: RMP1-14; Bio X Cell) at 200 μg/mouse twice a week, or SB 290157 and PMX205 as described in the E0771 model, or the combination of anti-PD-1 antibody with SB 290157 and PMX205.

Real-Time Impedance Assay: The human TIL in vitro killing assay was performed using a real-time impedance assay using a Real Time Cell Analysis (RTCA) S16 (ACEA Biosciences). Primary autologous cancer cells ($1.5\times10^4$ cells/well) were seeded in an E-plate 16 and cultured for 2 days. The TILs were in vitro—expanded for 21 days and stimulated with anti-CD3/CD28 antibodies for 24 hours. Effector cells were added into each well cultured with tumor cells at a ratio of 20:1 (effectorcell:cancer cell). Cancer cells and effector cells were co-cultured in a 37° C. CO2 incubator, and real-time monitored by RTCA S16.

Adoptive Cell Transfer: CD4+ and CD8+ T cells were negatively enriched using EasySepmouse CD4+ T-cell and EasySep mouse CD8+ T Enrichment Kits (Stemcell Technologies). One million mixed CD4+ and CD8+ T cells (2:1) were transferred by i.v. injection into 6-to-8-week-old gender matched recipient mice. After 14 days of T-cell transfer, recipient mice were implanted s.c. with B16F10 melanoma, and tumor growth was monitored daily.

Generation of PD-L1-Deficient Stable Cell Line Using CRISPR/Cas9-Mediated Gene Editing: B16 cells were cultured in complete DMEM medium. Cells were passaged every 2 to 3 days with a ratio of 1:6 to 1:8. pLentiCRISPR V1 plasmid was a gift from Feng Zhang (Addgene plasmid #49535. Current version is pLentiCRISPR V2, plasmid #52961). Cas9 guide sequence for mouse PD-L1 (NCBI Accession number: GQ904196) was designed as 5' AGCCTGCTGTCACTTGCTAC 3' (SEQ ID NO: 1) by the online program (crispr.mit.edu). The two oligos were synthesized from IDT as 5' CACCGAGCCTGCTGT-CACTTGCTAC 3' (SEQ ID NO: 2) and 5' AAOC GTAGCAAGTGACAGCAGGCTC 3' (SEQ ID NO: 3) (bold indicates the BsmBl restriction site). The pLentiCRISPR V1 was digested by the BsmBl, and the annealed oligos were cloned into pLentiCRISPR V1 according to the protocol from Zhang laboratory. To make the lentivirus, pLentiCRISPR (with cloned sgRNA) were cotransfected into HEK293(F)T cells with the packaging plasmids pVSVg (AddGene #8454) and psPAX2 (AddGene #12260). For PD-L1 silencing, CRISPR control or CRISPR sgRNA targeting PD-L1 viruses were transduced into B16F10 cells according to the protocol. The transduced B16F10 cells were selected in complete medium containing 1 μg/mL puromycin (Invivogen) 48 hours after transduction. The culture medium was replaced every 48 hours. The expression of PD-L1 was determined by flow cytometry. More detailed information regarding guide RNA design and construct cloning can be found at crispr.genomeengineering.org.

Primer List:
Mouse CPN1 (NM_030703)
Forward:
5' GGTGGACCTGAACCGCAACTTC 3' (SEQ ID NO: 12)
Reverse:
5' CGTTGGTGATGCCGTCTGGAA 3' (SEQ ID NO: 13)
Mouse β-Actin (NM_007393)
Forward:
5' ACCTTCTACAATGAGCTGCG 3' (SEQ ID NO: 15)
Reverse:
5' CTGGATGGCTACGTACATGG 3' (SEQ ID NO: 16)
C3a and C5a ELISA Complement C3a and C5a mouse ELISA kits (cat #ABIN415413 and ABIN415613) were purchased from Antibodies-Online. Tumors were carefully dissected from each mouse to keep them intact. The tumors were rinsed in cold PBS to remove blood thoroughly and weighed before homogenization. The tumors were then minced to small pieces and homogenized in PBS. The homogenates were centrifuged to obtain a cell-free supernatant. The quantities of C3a and C5a present in the supernatants, and in the medium from B16 cell culture, were determined by ELISA.

C3aR and C5aR Antagonists In Vitro Blockade: Mouse CD8+ T cells from lymph nodes were enriched using a negative selection kit (Stemcell Technologies; Cat #19853) and activated by plate-bound anti-CD3 (2 μg/mL) and anti-CD28 (1 μg/mL) antibodies for 72 hours. The activated CD8+ T cells were then cultured in complete medium alone (control), 10 μmol/L SB290157 (C3aR antagonist, C3aRA), 10 μmol/L PMX205 (C5aR antagonist, C5aRA), or a combination of 10 μmol/L SB290157 and 10 μmol/L PMX205 for 6 days. The IL10 expression was determined by intracellular staining.

Human Samples: Freshly isolated human hepatocarcinoma and lung cancer biopsies, as well as peripheral blood were provided by Hepatopancreatobiliary and Thoracic Surgery Departments, Beijing Cancer Hospital and Institute. The study was conducted in accordance with the Declaration of Helsinki and approved by the ethical committee of the Beijing Cancer Hospital and Institute. Patients signed an informed consent.

Statistical Analysis: Data are presented as mean±SEM. Results were analyzed by two-tailed Student t test or one-way ANOVA when multiple comparisons were made. Statistical significance was defined as $P \leq 0.05$.

Antibodies for Flow Cytometry and Cell Sorting: Anti-human CD3 (HIT3A), CD4 (A161A1), CD8 (HIT8A), IFNγ (4S.B3), TNFα (MAb11), C3aR (hC3aRZ8), C5aR (S5/1) antibodies and anti-mouse CD3 (17A2), CD4 (GK1.5), CD8 (53-6.7), CD11b (M1/70), CD11 c (N418), CD19 (6D5), CD25 (3C7), CD45.2 (104), TCRβ (H57-597), TCRγδ (UC7-13D5), F4/80 (BM8), IFNγ (XMG1.2), TNFα (MP6-XT22), IL-10 (DESS-16E3), GR1 (RB6-8C5), Ly6C (HK1.4), Ly6G (1A8), I-A/I-E (M5/114.15.2), NK1.1 (PK136), FOXP3 (MF-14), PD-1 (29F.1 A12), PD-L1 (10F.9G2) antibodies were purchased from Biolegend. Related isotype control antibodies were also from Biolegend. Primary anti-mouse C3aR antibody (D20) and goat IgG isotype control were purchased from Santa Cruz Biotechnology; and Alexa Fluor 488 donkey anti-goat secondary antibody was purchased from Life technologies. Fc receptors were blocked with mouse Fc receptor monoclonal antibody (2.4G2; BD PharMingen) before surface staining. CD45 was used for leukocyte gating and dead cells were detected using a LIVE/DEAD Fixable Dead Cell Stain Kit (Life Technologies) before cell surface staining in some experiments. For cytokine intracellular staining, cells were fixed and permeabilized using a Cytofix/Cytoperm kit (BD PharMingen) according to the manufacturer's instructions and then stained with IFNγ, TNFα or IL-10 monoclonal antibodies. Isotype control antibodies were used to distinguish background staining. FOXP3 Fix/Perm Buffer Set (Biolegend) was used for FOPX3 intracellular staining.

Human TILs Culture: Tumors were sliced with a sharp scalpel into small pieces (approximately 2 mm on each side). The fragments were immersed in 5 ml serum-free RPMI 1640 containing 1.5 mg/ml collagenase type II (Gibco, Cat #17101-015) and 10 μg/ml deoxyribonuclease type I (Sigma, Cat #DN25) and incubated for 2-3 hours at 37° C. with gentle agitation. The single-cell slurry was passed through sterile 70 μm mesh to remove undigested tissue chunks. The digested single-cell suspensions were washed twice in PBS, viable cells were purified on two step Ficoll gradient, and cells were resuspended for plating. Multiple wells of a 24-well plate were seeded with $1 \times 10^6$ viable cells in 2 mL culture medium with 6000 U/mL IL-2 and/or 100 U/ml IL-10. The plates were placed in a humidified 37° C. incubator with 5% $CO_2$. Once the lymphocyte growth was visible, half of the medium was replaced in all wells no later than 1 week after culture initiation. When any well became nearly confluent, the contents were mixed vigorously, split into two daughter wells, and filled to 2 mL per well with culture medium plus 6000 U/mL IL-2 and/or 100 U/ml IL-10. Subsequently, half the media was replaced at least twice weekly, or the cultures were split to maintain a cell density of 0.8 to $1.6 \times 10^6$ cells/mL. The TILs from digests that derived from individual wells of a 24-well plate were treated as an independent TIL culture and were maintained separately from the descendants of any other original well.

Generation of Stable Cell Lines: B16 cells were cultured in complete DMEM medium. Cells were passaged every 2-3 days with a ratio of 1:6 to 1:8. For CPN1 overexpression, CPN1 CDS was cloned into modified pLenti6.3 vector (Life technologies) and viruses were packaged according to the manufacturer's protocol. Transduced B16 cells were selected in complete medium containing 800 μg/ml G418 (Invivogen) 48 hrs after transduction. For CPN2 overexpression, CPN2 CDS was cloned into pLenti7.3 and viruses were packaged according to the manufacturer's protocol. GFP positive transduced B16F10 cells were sorted to generate a stable line.

Example 2

Regulation of IL-10 Expression in CD8+ T Cells by Complement

Figure 8A:
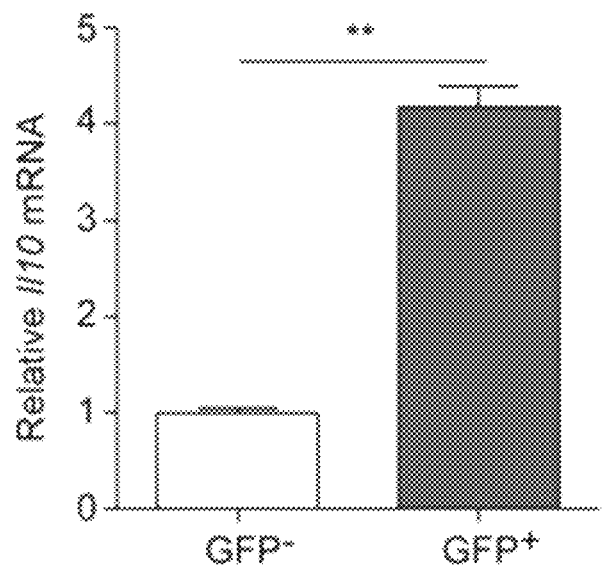
FIG. 8A shows relative 1110 mRNA level in GFP+ (IL-10) and GFP− CD8+ T cells.
Figure 8B:
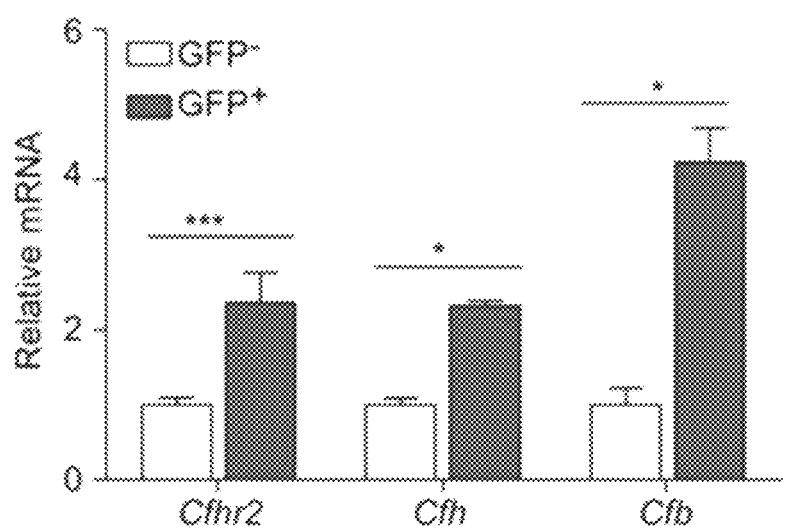
FIG. 8B shows relative mRNA levels in the genes which are related to the complement pathway. The data in FIG. 8A and FIG. 8B were generated by analyzing the microarray data set (GSE25846) of Trandem and colleagues (*Journal of Immunology*, 186:3642-52). For FIG. 8C, B16F10 melanoma cells (2×105/mouse) were subcutaneously inoculated into WT IL-10 reporter (Tiger) mice and C3−/− Tiger mice. The draining lymph nodes (dLNs) from tumor bearing mice were dissected and the GFP expression in the lymphocytes was analyzed by flow cytometry. Data represent a pool of 5-6 mice per group. Bars and error bars indicate mean±SEM. * p≤0.05, p≤0.01, *p≤0.001. Paired t-test.

To investigate the molecular regulation of IL-10 production in effector CD8+ T cells, gene expression profiles of IL-10+CD8+ T cells were analyzed based on data collected by Trandem and colleagues (*Journal of Immunology*, 186: 3642-52). FIG. 1A shows a heat map of the differentially expressed genes in IL-10+CD8+ T and IL-10−CD8+ T cells. The higher Il10 mRNA level in GFP+CD8+ T cells than that in GFP−CD8+ T cells indicates that GFP expression faithfully reflects IL-10 expression for this data set (FIG. 8A). Pathway analysis revealed that genes involved in the complement pathway were highly enriched among the genes differentially expressed between IL-10+ and IL-10−CD8+ T cells (FIG. 1B). The mRNA expression levels of several complement components and their receptors were upregulated in the IL-10+CD8+ T cells (FIGS. 1C and D). These data suggest that complement signaling pathways may be involved in the regulation of IL-10 expression in CD8+ T cells.

Figure 1D:
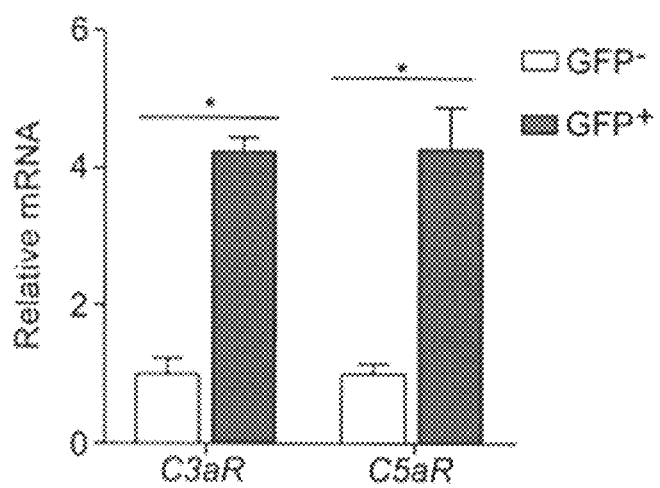
Figure 1E:
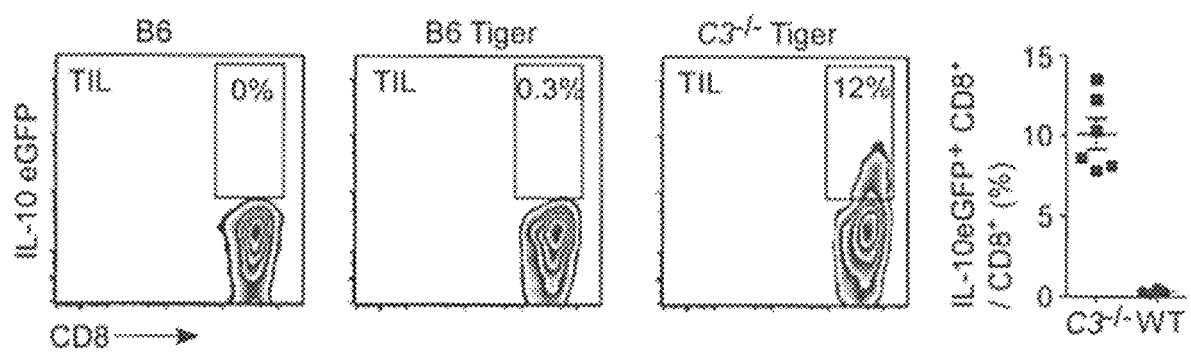
FIG. 1E shows expression of IL-10 in CD8+ TILs from wild-type (WT) and C3−/− mice. IL-10 reporter (Tiger) mice were crossed with C3−/− mice and inoculated with B16 melanoma cells. TILs were analyzed by flow cytometry from days 12 to 13. The percentages of IL-10+CD8+ TILs from six C3−/− Tiger mice are shown in the right plot. Error bars indicate SEM. Significance was determined in all panels by Student t test (*, P≤0.05; , P≤0.01; *, P≤0.001).
Figure 8C:
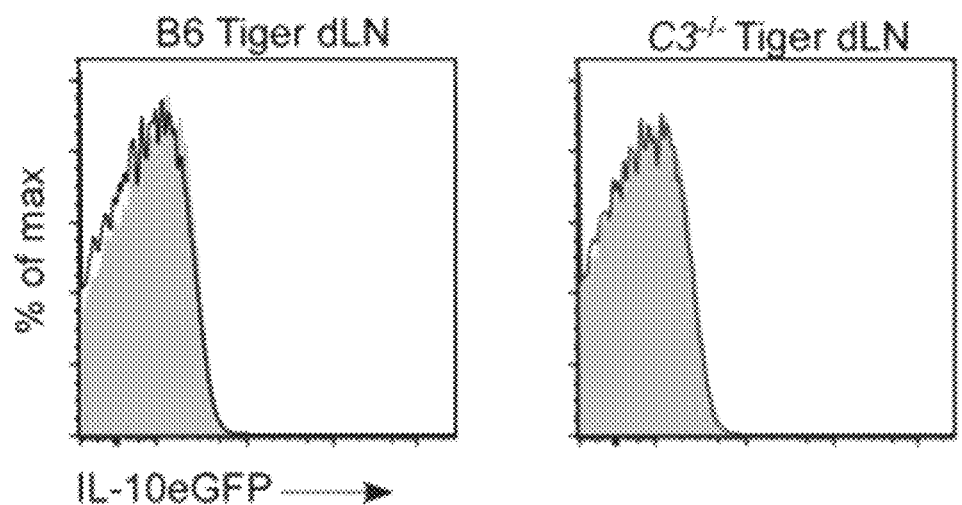
FIG. 8 shows regulation of IL-10 production in CD8+ TILs by complement.

To test whether complement signaling could regulate IL-10 production in effector CD8+ T cells during tumor development, Il10 reporter mice (termed Tiger mice), in which an IRES-GFP cassette was inserted between the stop codon and polyadenylation signal of the Il10 gene (as described by Kamanaka, et al., Immunity, 25(6):941-52 (2006)), were crossed with C3-deficient mice (as described by Wessels, et al., Proc. Natl. Acad. Sci. USA 92(25):11490-94 (1995)), and wild-type and C3−/−Il10 reporter mice were inoculated with B16 melanoma. IL-10 production in CD8+ TILs was measured. As shown in FIG. 1E, approximately 10% of CD8+ TILs expressed high levels of IL-10 in C3−/− mice, whereas no IL-10-producing CD8+ TILs were detected in the wild-type Tiger mice (FIG. 1E). CD8+ T cells in the draining lymph nodes (dLN) of either wild-type Tiger or C3−/− Tiger mice did not produce IL-10 (FIG. 8C). These data demonstrate that complement signaling inhibits IL-10 production in CD8+ TILs, and its removal is sufficient to promote IL-10 production in the tumor microenvironment but not in the periphery.

Example 3

Suppression of T-cell-Mediated Antitumor Immunity by Complement

Figure 2A:
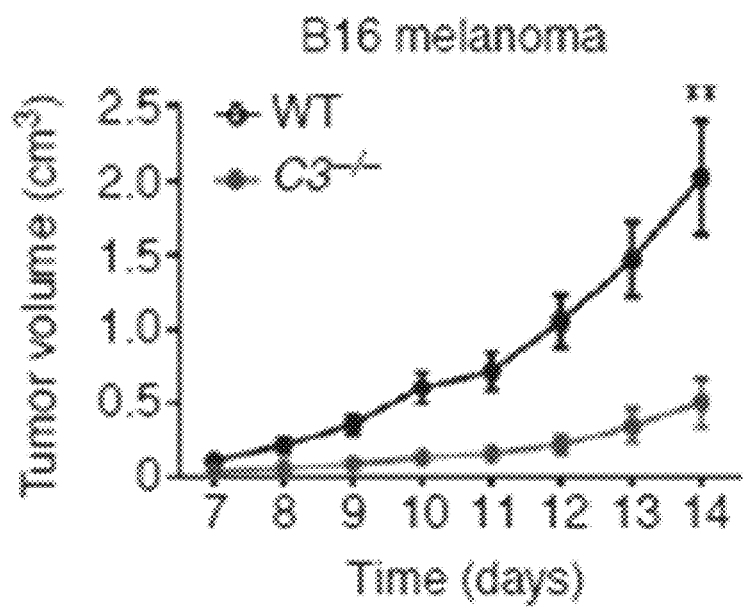
FIGS. 2A-C show melanoma development in C3−/− mice. B16F10 melanoma cells (2×10$^5$/mouse) were subcutaneously inoculated into wild-type (WT) and C3−/− mice. Tumor growth was monitored daily starting from day 7. Shown are tumor volume, size, and weight in these mice (n=9 mice per group).
Figure 2B:
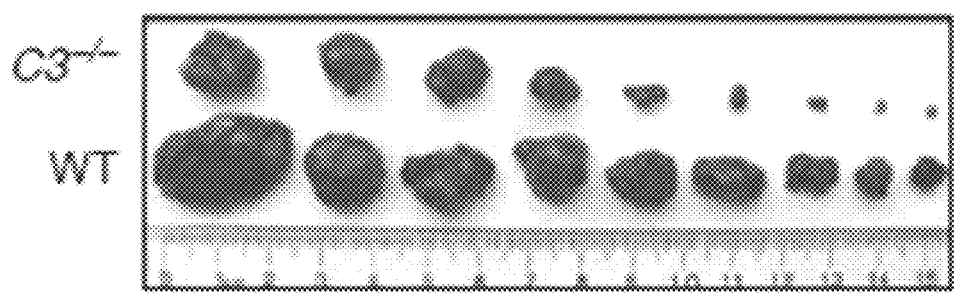
Figure 2C:
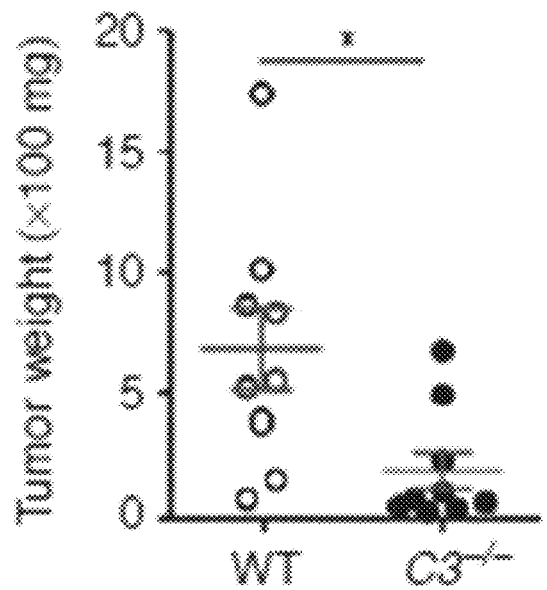

Melanoma Development in C3 Deficient Mice: B16F10 melanoma cells ($2 \times 10^5$/mouse) in 1004 PBS were subcutaneously inoculated into 6-8 week old wild-type (WT) and C3 knockout (C3−/−) mice. Tumor growth was monitored daily starting from day 7. B16 melanoma growth was dramatically slower in C3-deficient mice than that in wild-type mice (FIG. 2A-C). Specifically, C3-deficient mice displayed significantly smaller tumor volume (FIG. 2A), tumor size (FIG. 2B), and tumor weight (FIG. 2C) than WT controls.

Figure 2D:
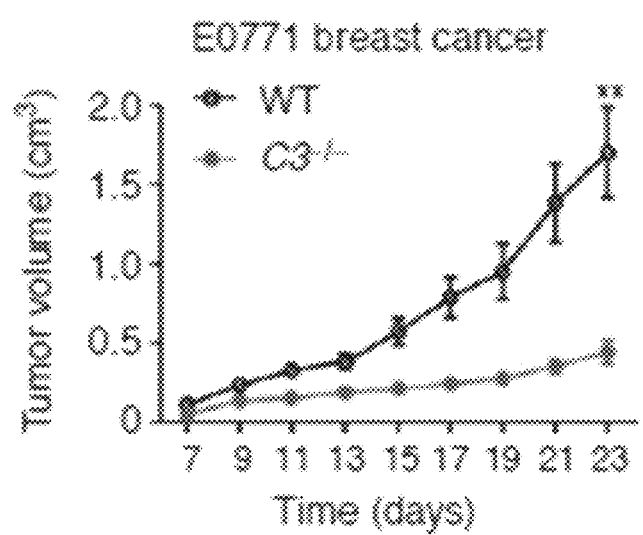
FIGS. 2D-F show breast cancer development in C3−/− mice. E0771 breast cancer cells (1×10$^6$/mouse) were subcutaneously inoculated into WT and C3−/− mice. Tumor growth was monitored every other day starting from day 7. Shown are tumor volume, size, and weight in these mice (n=9 mice per group).
Figure 2E:
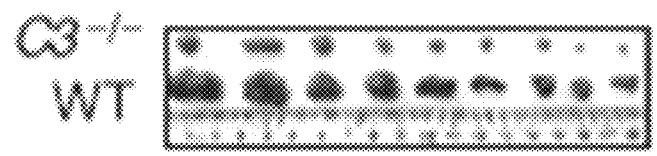
Figure 2F:
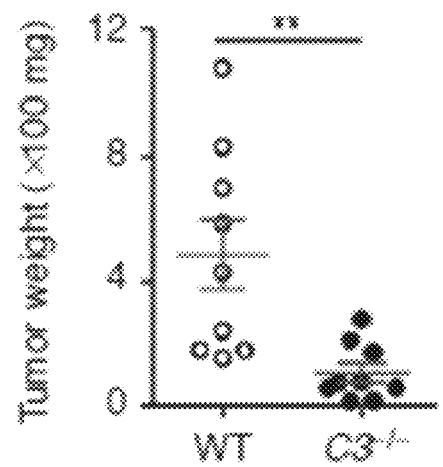

Breast Cancer Development in C3 Deficient Mice: E0771 breast cancer cells ($1 \times 10^6$/mouse) in 1004 PBS were subcutaneously inoculated into 6-8 week old wild-type (WT) and C3 knockout (C3−/−) mice. Tumor growth was monitored every other day starting from day 7. E0771 breast cancer development was dramatically slower in C3-deficient mice than that in wild-type mice (FIG. 2D-F). Specifically, C3-deficient mice displayed significantly smaller tumor volume (FIG. 2F), tumor size (FIG. 2G), and tumor weight (FIG. 2H) than WT controls.

Figure 2G:
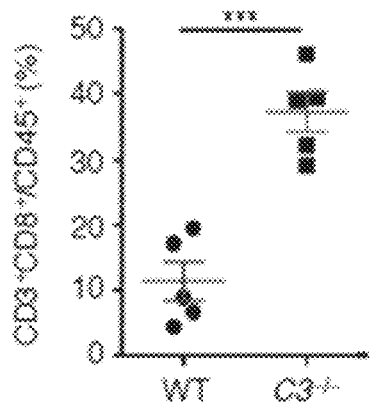
FIGS. 2G-H show phenotypes of CD8+ TILs from C3−/− mice. WT and C3−/− mice were subcutaneously inoculated with B16F10 cells (2×10$^5$/mouse). Total, IFNγ-, and TNFα-producing CD8+ TILs were analyzed by flow cytometry (n=5 mice per group) at day 12 after tumor inoculation.
Figure 2H:
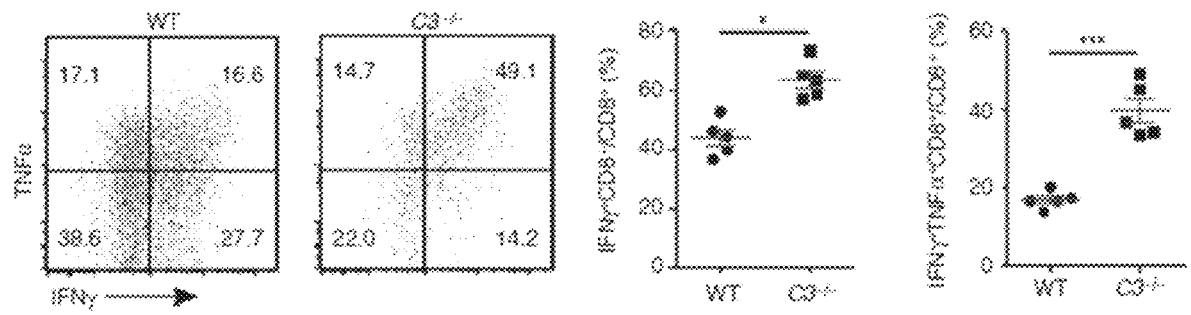
Figure 2I:
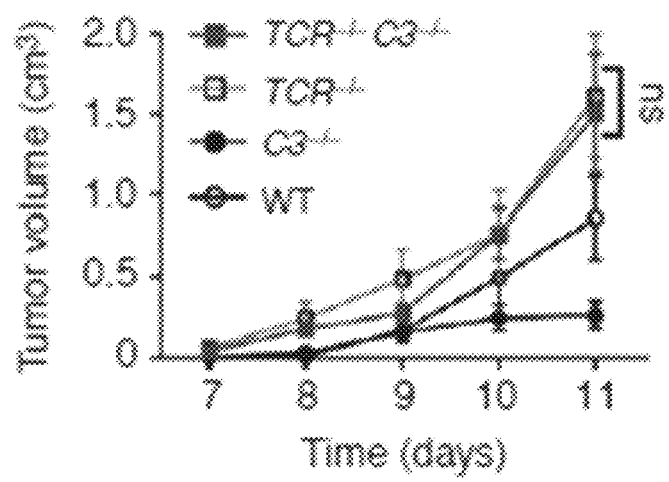
FIG. 2I shows B16F10 tumor development in WT, C3−/−, TCRα−/−, and C3−/− TCRα−/− mice (n=6 mice per group). All experiments shown are representative of at least three independent experiments. Bars and error bars indicate mean±SEM. Significance was determined in all panels by Student t test (ns, P>0.05; *, P≤0.05; , P≤0.01; *, P≤0.001).

Phenotypes of CD8+ TILs from C3−/− mice: WT and C3−/− mice were subcutaneously inoculated with B16F10 cells ($2 \times 10^5$/mouse). Total, IFNγ-, and TNFα-producing CD8+ TILs were analyzed by flow cytometry at day 12 after tumor inoculation. CD8+ T cells were the dominant cell population in TILs from C3−/− mice, representing an approximate 4-fold increase in their numbers compared with those from wild-type mice (FIG. 2G). These CD8+ TILs exhibited multipotency as demonstrated by a simultaneous increase in their IFNγ and TNFα expression (FIG. 2H). To further determine whether the enhanced antitumor response in C3−/− mice is T-cell—mediated, C3−/− mice were crossed with T cell receptor alpha chain knockout mice (TCRα−/−) lacking functionally mature T cells, and tumor growth in the C3−/−TCRα−/− mice was investigated. TCRα−/− mice had impaired antitumor immunity (FIG. 2I). Removal of mature T cells from C3−/− mice resulted in a complete loss of their tumor resistance (FIG. 2I). These results suggest that the enhanced antitumor immunity in C3−/− mice is mediated through the enhanced CD8+ CTL-mediated killing.

Example 4

Non-CD8+ T-cell Responses in Tumor-Bearing Mice

Figure 3A:
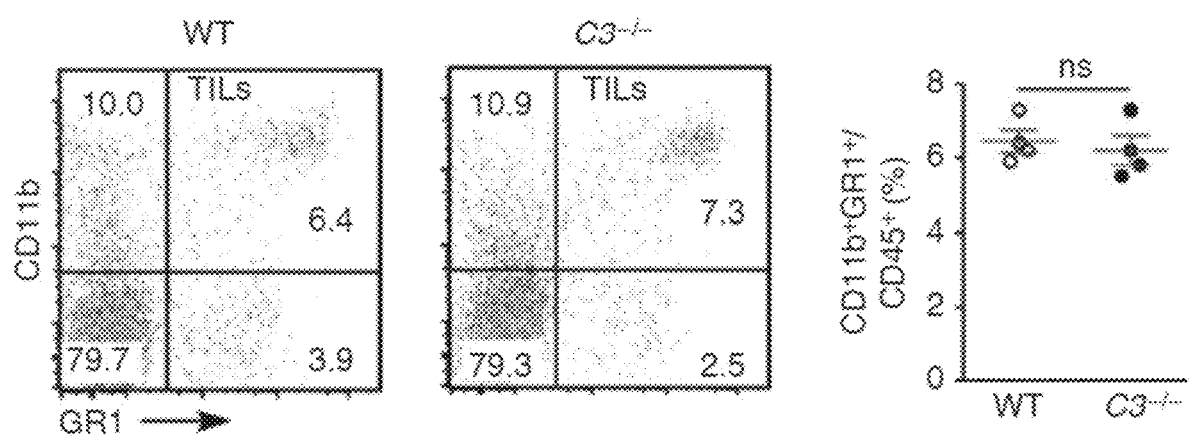
FIG. 3A shows flow cytometry analysis of CD11b and GR1 expression in leukocytes from tumor-infiltrating lymphocytes (TIL) (n=4 mice per group).
Figure 9A:
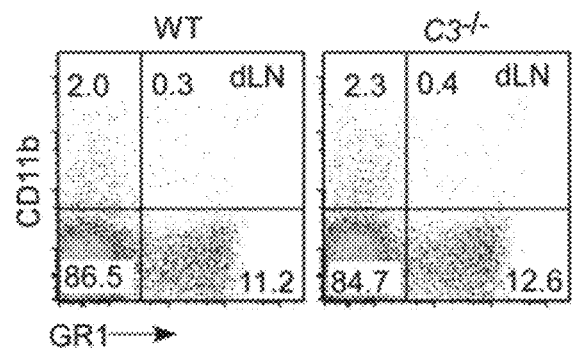
FIG. 9A show the CD11b and GR1expression in leukocytes from dLNs as analyzed by flow cytometry.

Recruitment of MDSCs: Complement may inhibit antitumor immunity by recruiting myeloid-derived suppressor cells (MDSCs) to the tumor site or by preventing NK activation. To investigate the role of complement signaling in MDSC recruitment and NK activation, B16F10 melanoma cells ($2 \times 10^5$/mouse) were subcutaneously inoculated into wild-type (WT) and C3−/− mice. The draining lymph nodes (dLNs) and tumors were treated with collagenase and DNase to generate a single-cell suspension. Leukocytes were pregated on CD45+ cells and MDSCs were quantified. Comparable numbers of myeloid cells in the dLNs of both types of mice were observed (FIG. 9A). FIG. 3A shows flow cytometry analyses of CD11b and GR1 expression in leukocytes from tumor-infiltrating lymphocytes (TIL) (n=4 mice per group). The percentages of CD11b+GR1+ cells, which contain both $CD11b^{hi}GR1^{hi}$ neutrophils and CD11b+ $GR1^{dim}$ MDSCs, were comparable in tumor-infiltrating leukocytes from the tumors growing in either wild-type or C3−/− mice. Most of these cells were $CD11b^{hi}GR1^{hi}$ neutrophils. These data suggest that MDSC-mediated immunosuppression might not be a major cellular mechanism in B16 melanoma in C3−/− mice.

Figure 3B:
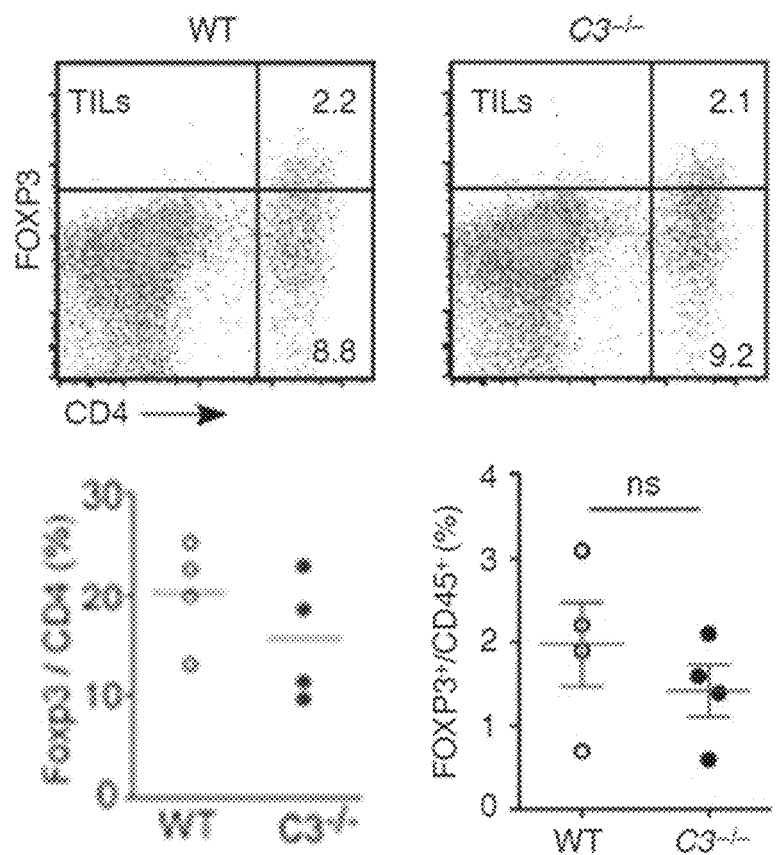
FIG. 3B shows flow cytometry analysis of the regulatory CD4+ T-cell population in leukocytes from TILs using CD4 and FOXP3 as markers (n=4 mice per group).
Figure 9B:
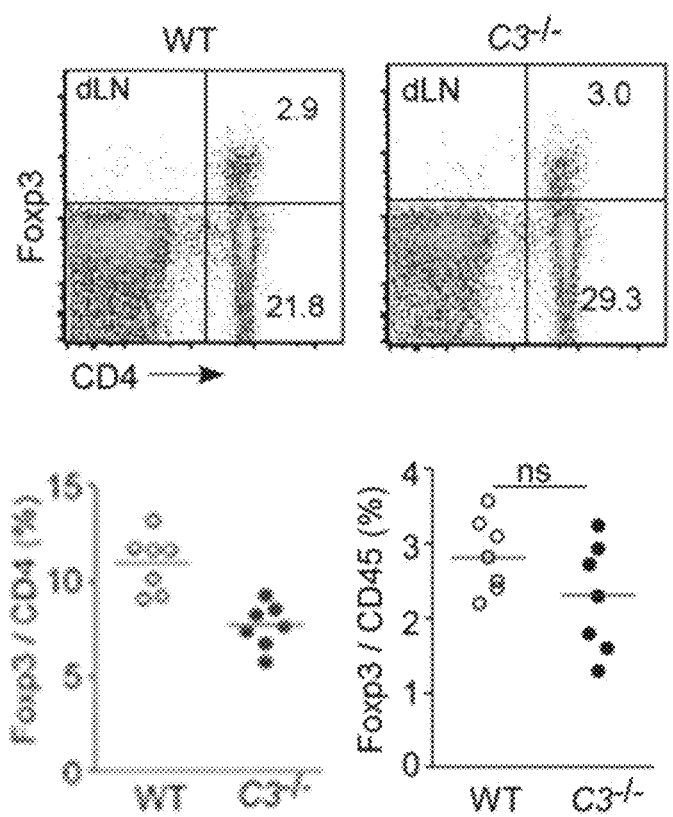
FIG. 9B shows regulatory CD4+ T cell population in leukocytes from dLNs were as analyzed by flow cytometry using CD4 and Foxp3 as markers.

Treg Expansion: Expanded regulatory T cells (Tregs) in DLNs and TILs are associated with tumor immunosuppression. To investigate the role of complement signaling in Treg expansion, B16F10 melanoma cells ($2 \times 10^5$/mouse) were subcutaneously inoculated into wild-type (WT) and C3−/− mice. The draining lymph nodes (dLNs) and tumors were treated with collagenase and DNase to generate a single-cell suspension. Leukocytes were pregated on CD45+ cells. FIG. 3B shows flow cytometry analysis of the regulatory CD4+ T-cell population in leukocytes from TILs using CD4 and FOXP3 as markers (n=4 mice per group). No difference was found in the percentage of Tregs in dLNs or TILs from wild-type and C3−/− mice (FIG. 3B and FIG. 9B).

Figure 3C:
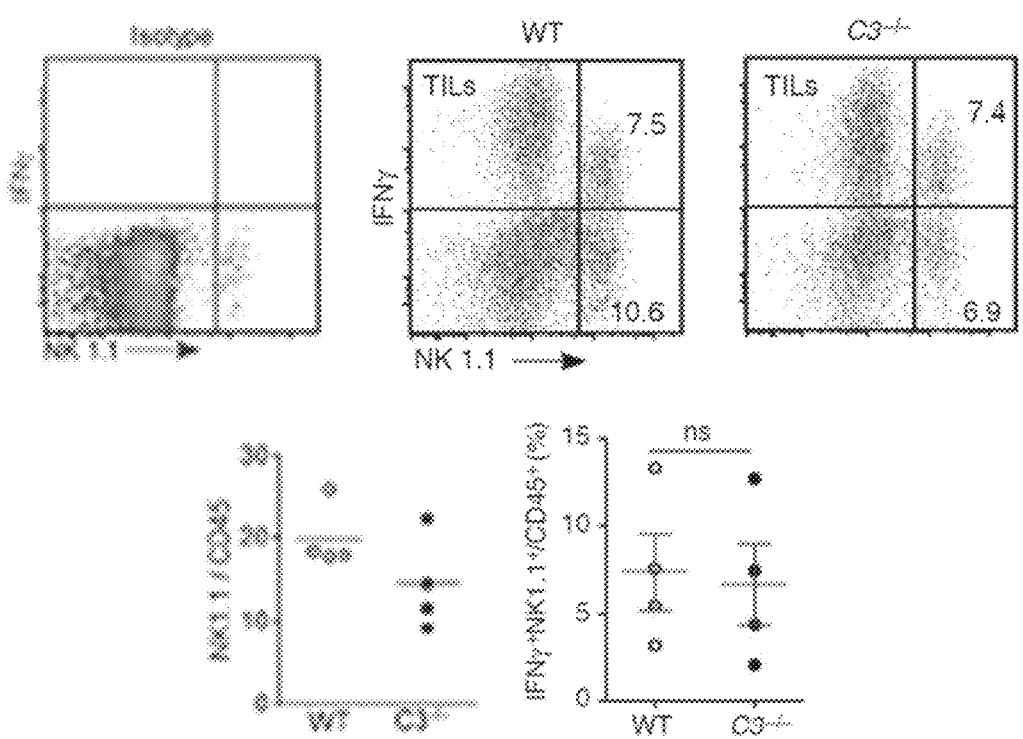
FIG. 3C shows flow cytometry analysis of the natural killer cell (NK) population in leukocytes from TILs using NK1.1 as a marker (n=4 mice per group). Experiments shown are representative of three independent experiments. Bars and error bars indicate mean±SEM. Significance was determined in all panels by Student t test (ns, P>0.05).
Figure 9C:
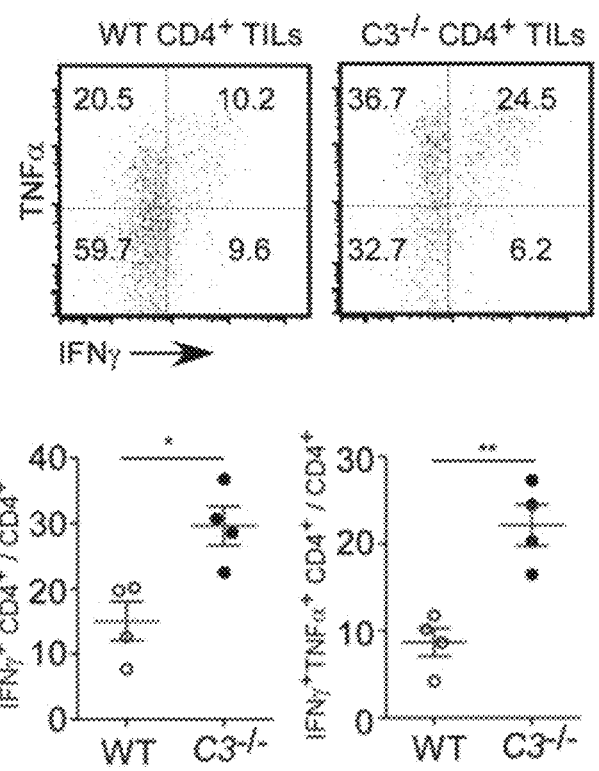
FIG. 9C shows phenotypes of CD4+ TILs from C3−/− mice. WT and C3−/− mice were subcutaneously inoculated with B16F10 cells (2×10$^5$/mouse). IFNγ- and TNFα-producing CD4+ TILs were analyzed by flow cytometry (n=4 mice per group) at day 12 after tumor inoculation.
Figure 9D:
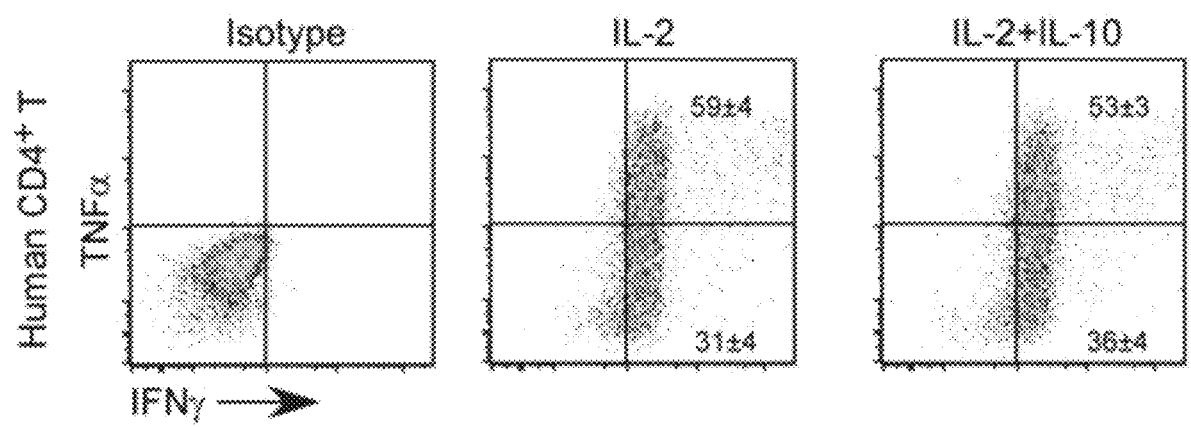
FIG. 9D shows the impact of IL-10 on effector cytokine production in human CD4+ T cells. CD4+ T cells were enriched from PBMCs of healthy donors and activated by anti-CD3/CD28 antibodies in vitro for 48 hrs. The activated CD4+ T cells were then cultured with 100 U/ml rIL-2 or 100 U/ml rIL-2 plus 500 U/ml rIL-10 for 48 hrs. The cells were activated using a Cell Activation Cocktail (Biolegend) for 6 hours before intracellular IFNγ and TNFα staining. The expression of IFNγ and TNFα was analyzed by flow cytometry (n=3).
Figure 9E:
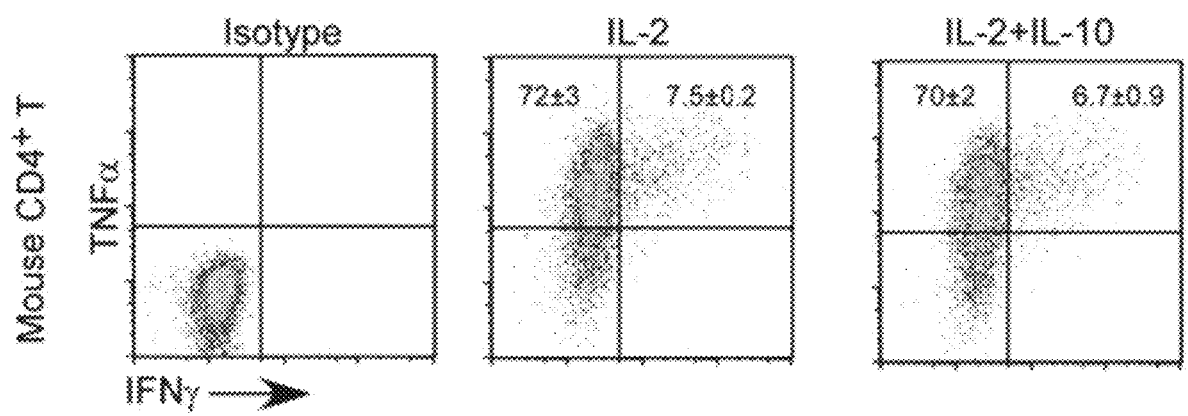
FIG. 9E shows the impact of IL-10 on effector cytokine production in mouse CD4+ T cells. Mouse CD4+ T cells were enriched from the spleens of naïve mice using a negative selection kit and activated by anti-CD3/CD28 antibodies for 48 hours in vitro. The activated CD4+ T cells were then cultured with 100 U/ml rIL-2 or 100 U/ml rIL-2 plus 500 U/ml rIL-10 for 48 hrs. The cells were activated using a Cell Activation Cocktail (Biolegend) for 6 hours before intracellular IFNγ and TNFα staining. The expression of IFNγ and TNFα was analyzed by flow cytometry (n=3). Data shown are representative of three independent experiments. Bars and error bars indicate mean±SEM. ns, p>0.05, *p≤0.05, **p≤0.01. Student's t-test.

Although the percentage of CD4+ TILs was comparable between wild-type and C3−/− mice, more CD4+ TILs from C3−/− mice expressed effector cytokines (FIG. 9C). To test the direct impact of IL-10 on CD4+ T-cell function, CD4+ T cells were enriched from PBMCs of healthy donors and activated by anti-CD3/CD28 antibodies in vitro for 48 hrs. The activated CD4+ T cells were then cultured with 100 U/ml rIL-2 or 100 U/ml rIL-2 plus 500 U/ml rIL-10 for 48 hrs. The cells were activated using a Cell Activation Cocktail (Biolegend) for 6 hours before intracellular IFNγ and TNFα staining. IL-10 did not obviously alter the effector status of either human or mouse CD4+ T cells in vitro (FIG. 9D-E). These results suggest that the enhanced effector phenotype in CD4+ TILs is likely due to an indirect effect in the tumors from C3−/− mice. Furthermore, the percentage of total or activated NK cells in the TILs from C3−/− mice did not change compared with wild-type mice (FIG. 3C). In addition, no difference in the cell populations of NK cells, Th17 cells, macrophages, or dendritic cells in the tumor-infiltrating leukocytes between wild-type and C3−/− mice was observed.

Example 5

Role of IL-10 in Antitumor Response in C3−/− Mice

Figure 4A:
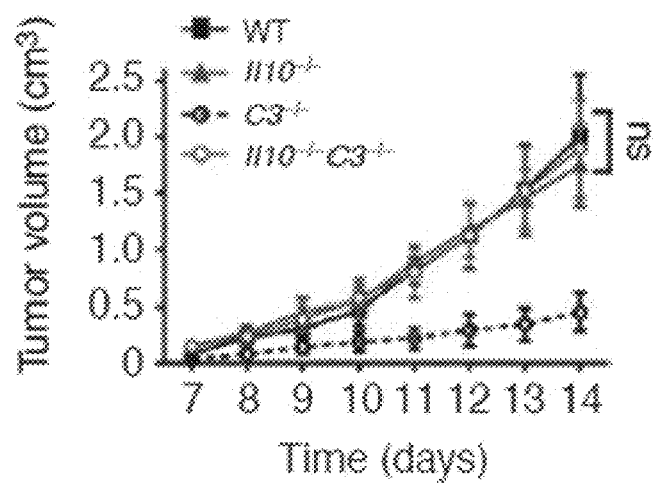
FIGS. 4A-C show melanoma development in C3−/− mice. B16F10 melanoma cells (2×10$^5$/mouse) were subcutaneously inoculated into wild-type (WT), IL-10−/−, C3−/−, and IL-10−/−C3−/− mice. Tumor growth was monitored daily starting from day 7. Shown are tumor volume, size, and weight in these mice (n=8 mice per group).
Figure 4B:
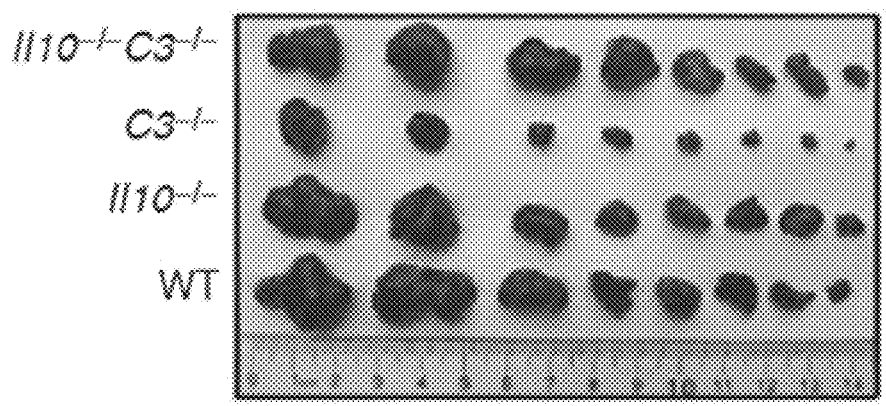
Figure 4C:
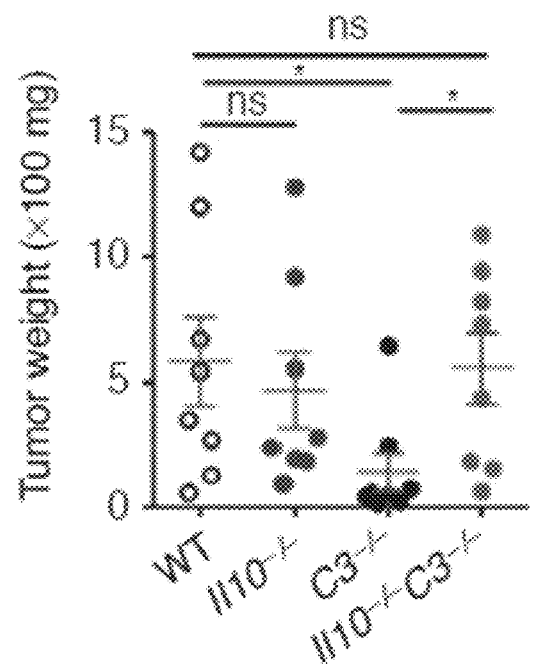
Figure 4D:
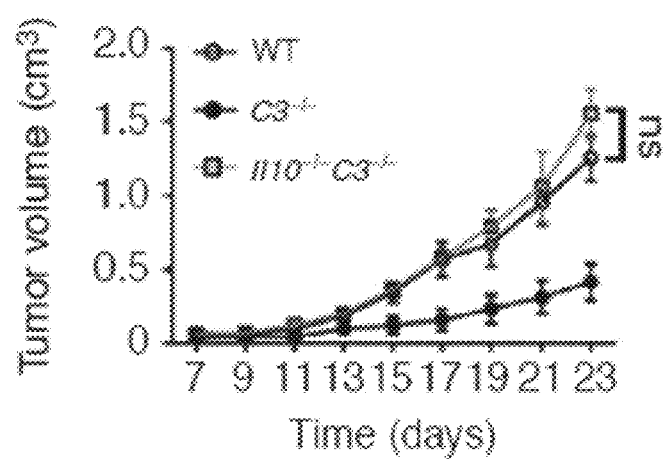
FIGS. 4D-F show breast cancer development in C3−/− mice. E0771 breast cancer cells ($1\times10^6$/mouse) were subcutaneously inoculated into WT, C3−/−, and IL-10−/−C3−/− mice. Tumor growth was monitored every other day starting from day 7. Shown are tumor volume, size, and weight in these mice (n=8 mice per group). All experiments shown are representative of three independent experiments. Bars and error bars indicate mean±SEM. Significance was determined by Student t test in A and D, and by ANOVA in C and F (ns, P>0.05; *, P≤0.05; **, P≤0.01).
Figure 4E:
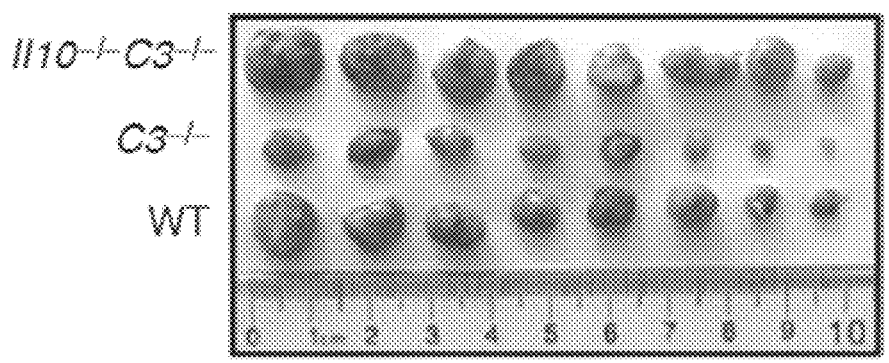
Figure 4F:
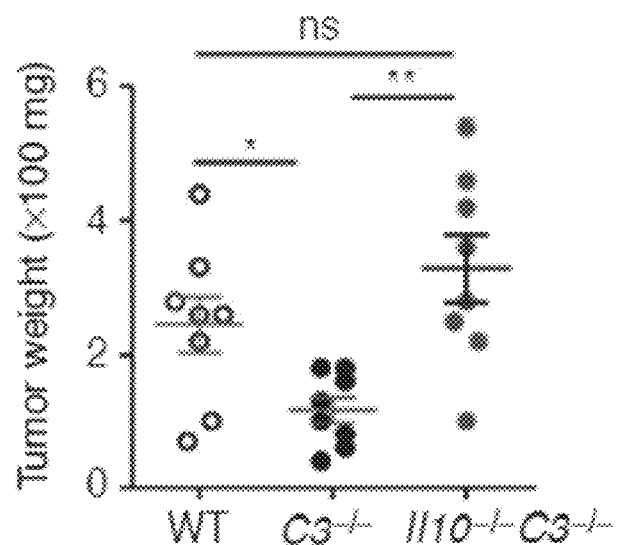

To determine whether IL-10 is essential for the enhanced antitumor immunity in C3−/− mice, C3−/− mice were crossed with IL-10−/− mice to generate double-mutant mice. Mice were subcutaneously inoculated with B16F10 melanoma cells ($2\times10^5$/mouse) or E0771 breast cancer cells ($1\times10^6$/mouse), and tumor development was examined. Deletion of IL-10 in C3−/− mice completely abolished their enhanced tumor resistance to B16 melanoma (FIG. 4A-C) as well as E0771 breast cancer (FIG. 4D-F). However, IL-10 deletion in the wild-type background did not result in altered antitumor immunity compared with wild-type mice (FIG. 4A-C), suggesting that IL-10 may not be involved in antitumor immunity in these tumor models when complement signaling is intact, as the complement signaling prevents IL-10 production in CD8+ TILs.

Example 6

Enhanced Human TIL Function by IL-10

To determine whether recombinant human IL-10 could enhance the function of TILs from patients with cancer, TILs were isolated from human lung tumors and cultured in the presence of IL-2, or IL-2 and IL-10. Tumors were sliced with a sharp scalpel into small pieces (approximately 2 mm on each side). The fragments were immersed in 5 ml serum-free RPMI 1640 containing 1.5 mg/ml collagenase type II (Gibco, Cat #17101-015) and 10 μg/ml deoxyribonuclease type I (Sigma, Cat #DN25) and incubated for 2-3 hours at 37° C. with gentle agitation. The single-cell slurry was passed through sterile 70 μm mesh to remove undigested tissue chunks. The digested single-cell suspensions were washed twice in PBS, viable cells were purified on two step Ficoll gradient, and cells were resuspended for plating. Multiple wells of a 24-well plate were seeded with $1\times10^6$ viable cells in 2 mL culture medium with 6000 U/mL IL-2 and/or 100 U/ml IL-10. The plates were placed in a humidified 37° C. incubator with 5% $CO_2$. Once the lymphocyte growth was visible, half of the medium was replaced in all wells no later than 1 week after culture initiation. When any well became nearly confluent, the contents were mixed vigorously, split into two daughter wells, and filled to 2 mL per well with culture medium plus 6000 U/mL IL-2 and/or 100 U/ml IL-10. Subsequently, half the media was replaced at least twice weekly, or the cultures were split to maintain a cell density of 0.8 to $1.6\times10^6$ cells/mL. The TILs from digests that derived from individual wells of a 24-well plate were treated as an independent TIL culture and were maintained separately from the descendants of any other original well.

Figure 5A:
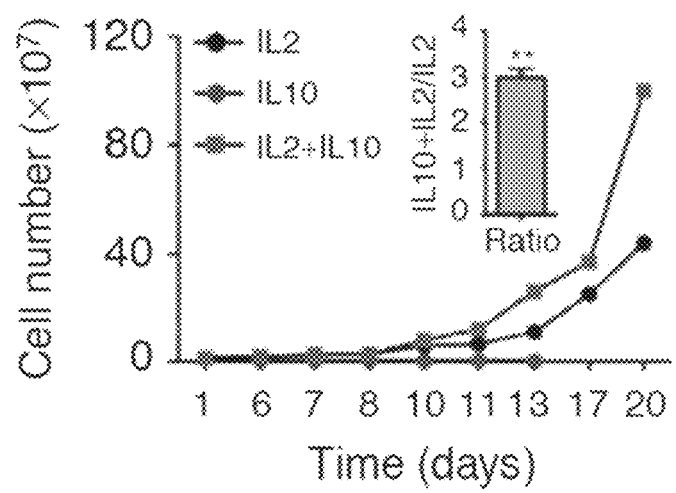
FIG. 5A shows cell number of in vitro—expanded TILs from patients with lung cancer. TILs were isolated and cultured in the presence of 6,000 U/mL rIL-2, 100 U/mL rIL-10, or 6,000 U/mL rIL-2 plus 100 U/mL rIL-10. The numbers of live TILs counted are shown (y-axis). The inserted panel shows the ratio of TILs from two types of culture from 3 patients.
Figure 5B:
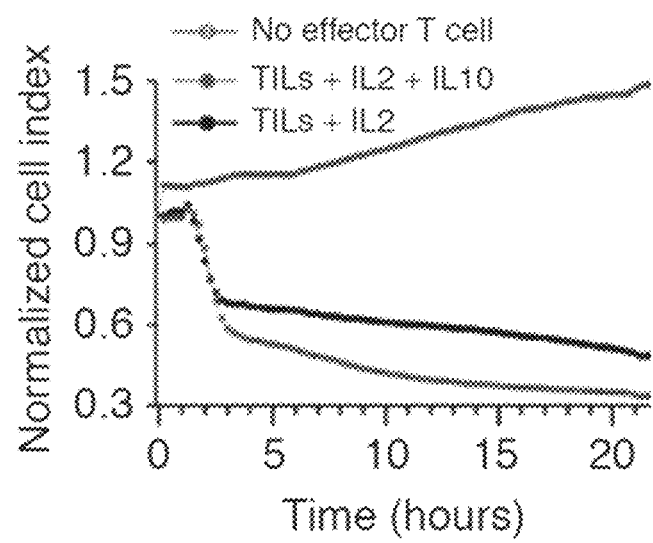
FIG. 5B shows the killing activity of in vitro—expanded TILs. The expanded TILs in FIG. 5A were activated by anti-CD3/CD28 antibodies for 24 hours and tested for their ability to kill autologous primary tumor cells at an Effector:Target ratio of 20:1. The killing activity was measured at 15-minute intervals by Impedance assay.
Figure 5C:
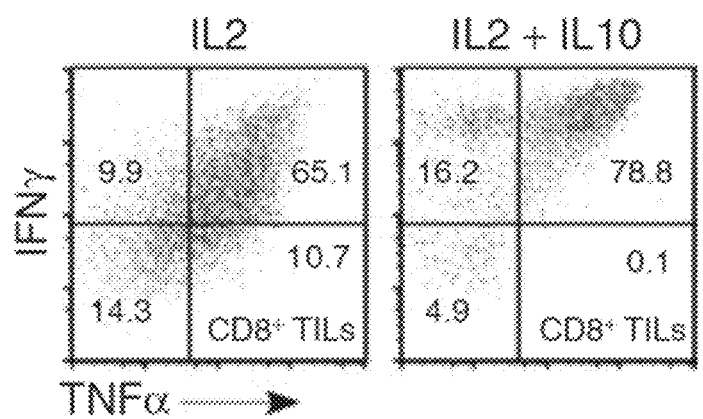
FIGS. 5C-D show IFNγ and TNFα expression in CD8+ TILs expanded in vitro. TILs from lung cancers were expanded in complete culture medium with 6,000 U/mL rIL-2 alone or combined with 100 U/mL rIL-10 for 20 days. IFNγ and TNFα expression in CD8+ TILs was analyzed by flow cytometry. Results shown in FIGS. 5A-D are representative of 3 to 6 patients.
Figure 5D:
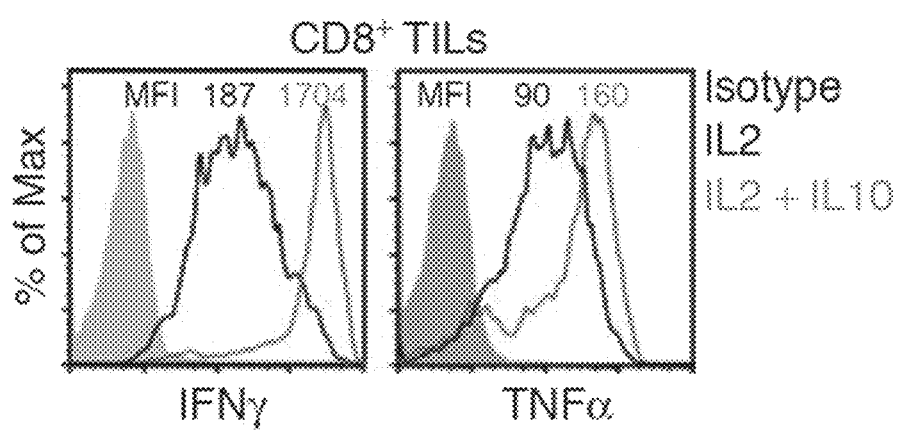
Figure 10:
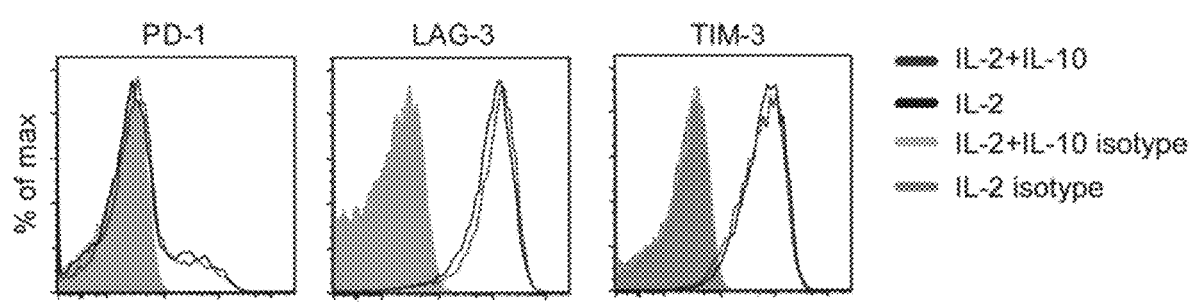
FIG. 10 shows T cell exhaustion markers expressed on CD8+ TILs after IL-10 culture. Human TILs from lung cancer patients were isolated and cultured for 21 days in vitro with IL-2 or IL-2 plus IL-10. T cells were activated by anti-CD3/CD28 antibodies for 24 hrs. The surface expression of PD-1, LAG-3 and TIM-3 was analyzed by flow cytometry. FACS profiles are representative of three patients.

As shown in FIG. 5A, TILs started to expand and enter logarithmic growth phase after 2 weeks of culture in the presence of IL-2. IL-10 robustly enhanced the proliferative capacity of TILs when added with IL-2, whereas IL-10 alone did not drive TILs into the cell cycle (FIG. 5A). To test the tumor killing of the expanded TILs directly, in vitro—expanded TILs were co-cultured with autologous primary tumors. Compared with IL-2-expanded TILs, TILs expanded by IL-2 plus IL-10 induced a rapid and more effective killing of primary tumor cells (FIG. 5B). Furthermore, CD8+ TILs expanded in vitro with IL-2 plus IL-10 had a much enhanced expression of IFNγ and TNFα (FIGS. 5C and D). However, the expression of T-cell exhaustion markers, such as programmed death 1 (PD-1), LAG3, and TIM3, was not altered by IL-10 (FIG. 10). Together, these results suggest that IL-10 may be applied as a T-cell growth factor for in vitro expansion of human TILs.

Figure 5E:
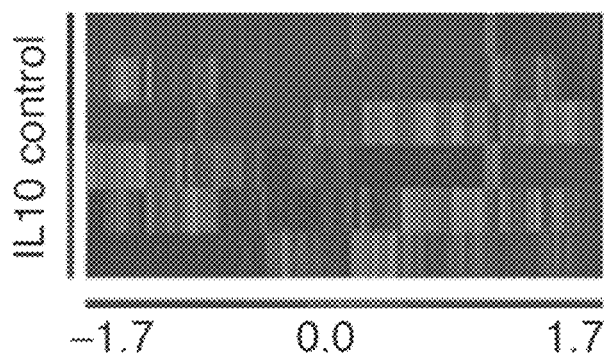
FIG. 5E shows a heat map of the differentially expressed genes in IL-10-treated human lung tumor CD8+ TILs.
Figure 5F:
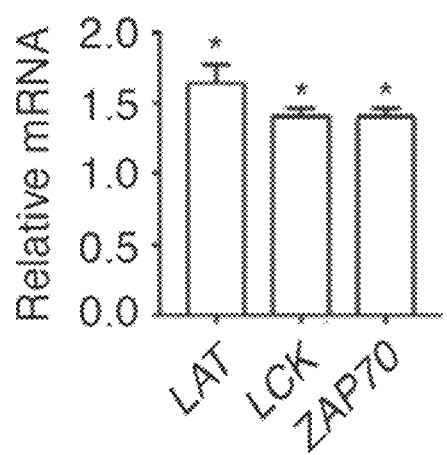
FIGS. 5F-J show mRNA expression of different pathways as indicated in IL-10/IL-2—treated human CD8+ TILs. Plotted are relative expression levels of mRNAs compared with those from IL-2-treated cells for each indicated gene based on gene chip data. Shown are the mean±SEM. Significance was determined by ANOVA in FIGS. 5F-J (*, P≤0.05; **, P≤0.01).
Figure 5G:
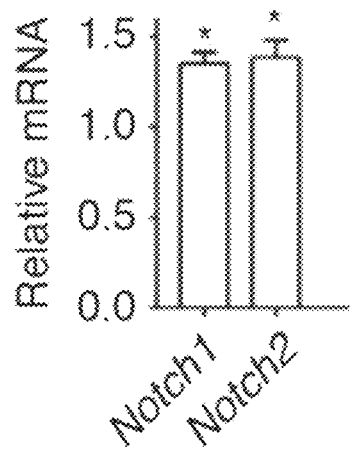
Figure 5H:
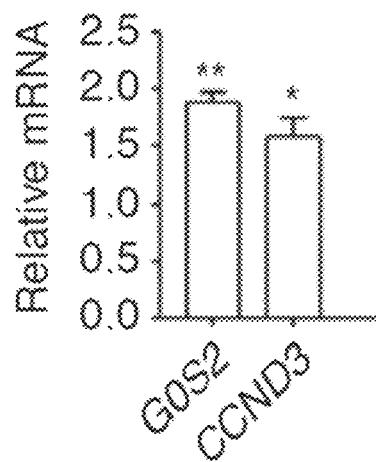
Figure 5I:
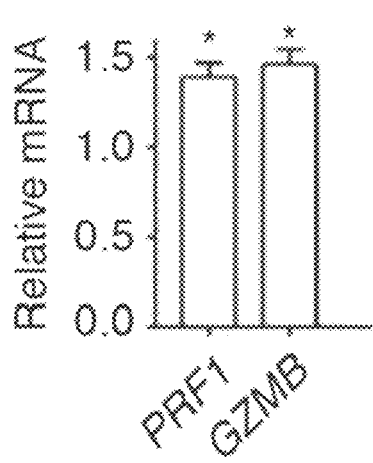
Figure 5J:
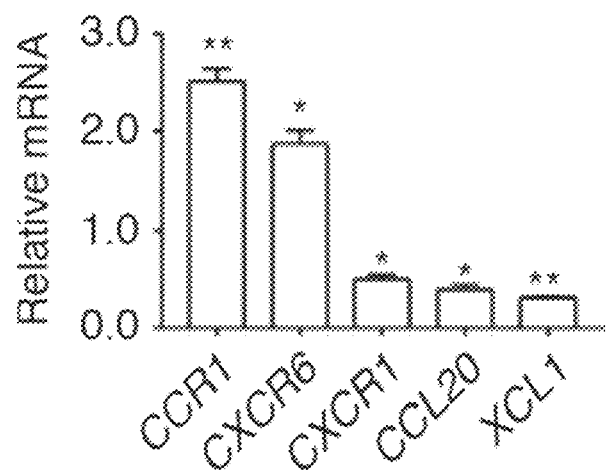

To further understand how IL-10 promotes human CD8+ TIL function, an mRNA expression profiling assay was performed in IL-2-expanded CD8+ TILs from human lung tumors with or without IL-10. IL-10/IL-2-cultured CD8+ TILs displayed a different gene expression pattern compared with that in IL-2-cultured CD8+ TILs (FIG. 5E). IL-10 upregulated genes related to several signaling pathways, including T-cell receptor (TCR) signaling (FIG. 5F), Notch signaling (FIG. 5G), cell cycle (FIG. 5H), and killing activity (FIG. 5I). The effect of IL-10 on the expression of chemokine genes was variable depending on the specific chemokine (FIG. 5J). These data indicate that IL-10 stimulation induces potent effector function in human TILs and elicits distinct signaling pathways. These data also indicate that IL-10 plays a similar role in human and mouse CD8+ T cells.

Example 7

Suppression of IL-10 Production by Autocrine C3

Figure 6A:
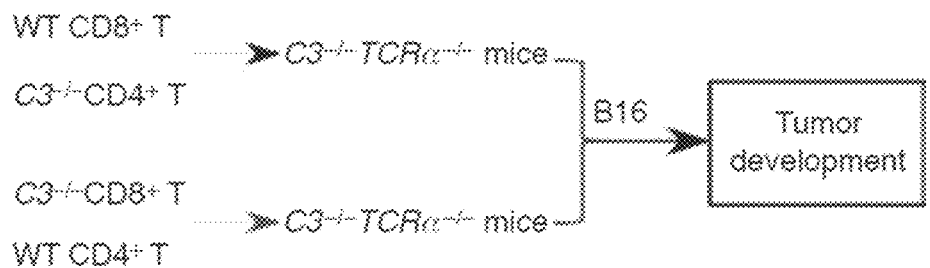
FIG. 6A shows a schematic of T-cell transfer to C3−/−TCR−/− mice and tumor development.
Figure 6B:
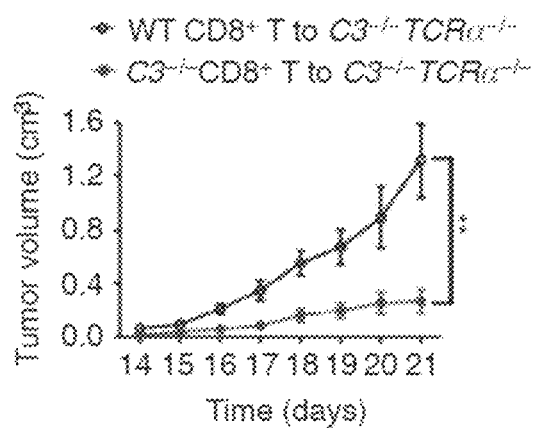
FIG. 6B shows melanoma development in chimeric mice. B16F10 melanoma cells were inoculated into T-cell—reconstituted C3−/−TCR−/− mice, and tumor development was monitored daily (n=5 mice per group).

To determine whether endogenous C3 expressed by CD8+ T cells inhibits their IL-10 production, CD4+ and CD8+ T cells from wild-type or C3−/− naïve mice were transplanted into C3−/−TCRα−/− recipients and mice were inoculated with B16 melanomas (FIG. 6A). Tumors in mice receiving C3−/− CD8+ T cells developed more slowly than those in mice receiving wild-type CD8+ T cells (FIG. 6B), indicating that complement C3 expressed by CD8+ T cells inhibits their antitumor activity through an autocrine mechanism. In addition, C3aR and C5aR transcripts were upregulated in IL-10-producing effector CD8+ T cells (FIG. 1D).

Figure 6C:
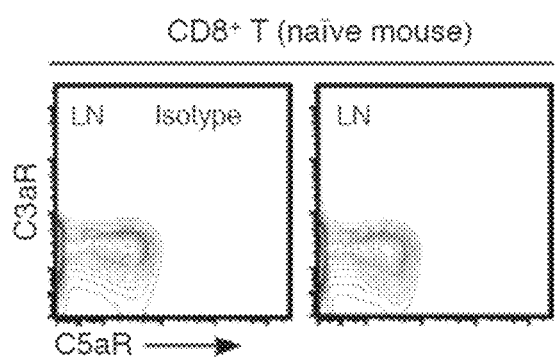
FIG. 6C shows fluorescence activated cell sorting (FACS) profiles of C3aR and C5aR expression on CD8+ T cells from dLNs of naïve mice.
Figure 6D:
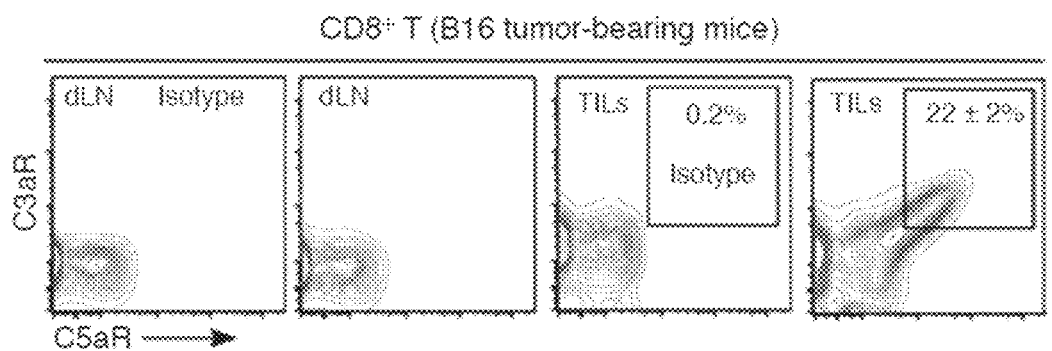
FIG. 6D shows FACS profiles of C3aR and C5aR expression on CD8+ T cells from dLNs and melanomas. B16F10 melanoma cells ($2\times10^5$/mouse) were subcutaneously inoculated into wild-type (WT) mice, and TILs were isolated at day 13 and analyzed by flow cytometry.
Figures 6E, 6F:
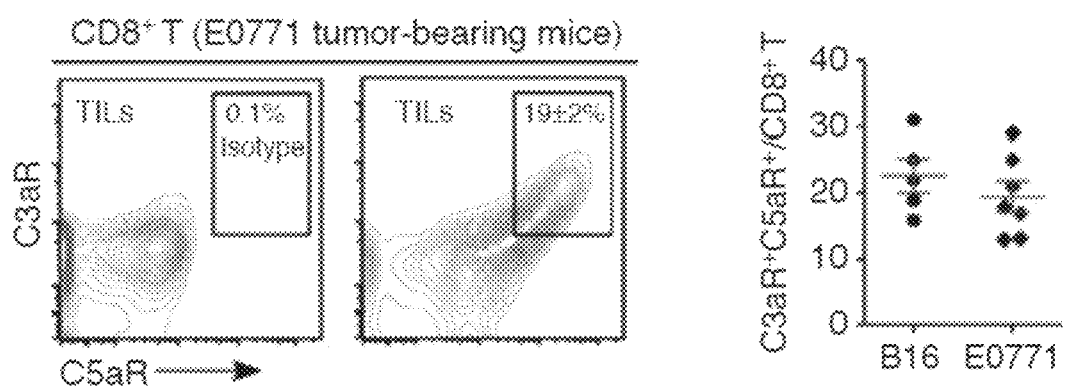
FIG. 6E shows FACS profiles of C3aR and C5aR expression on CD8+ T cells from breast cancer. E0771 cells ($1\times10^6$/mouse) were subcutaneously inoculated into WT mice. The expression of C3aR and C5aR on CD8+ TILs was analyzed at day 19 by flow cytometry.
FIG. 6F shows a summary of results from 6D-E.
Figure 6G:
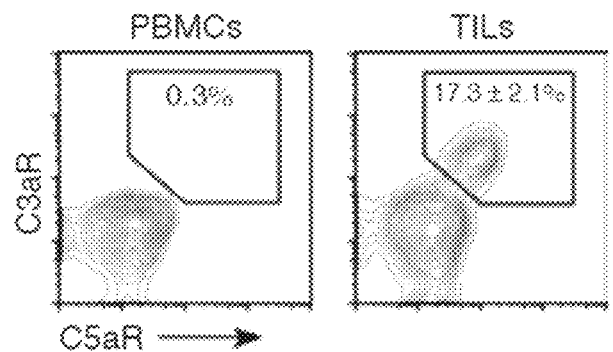
FIG. 6G shows FACS profiles of C3aR and C5aR expression on CD8+ cells from peripheral blood mononuclear cells (PBMC) and TILs from liver cancer (n=5).

Surface expression of C3aR and C5aR on CD8+ TILs was examined. Peritoneal macrophages and splenic neutrophils, which express high levels of C3aR and C5aR (FIGS. 11A-B), were used as controls. CD8+ T cells from dLNs of naïve mice or tumor-bearing mice did not express C3aR or C5aR (FIGS. 6C and D, left two plots). However, approximately 20% of the CD8+ TILs from melanomas expressed C3aR and C5aR (FIG. 6D, right two plots). A similar percentage of CD8+ TILs from an E0771 breast cancer model also expressed C3aR and C5aR (FIG. 6E-F). Moreover, CD8+ TILs isolated from human liver tumors expressed high levels of C3aR and C5aR (FIG. 6G).

Figure 6H:
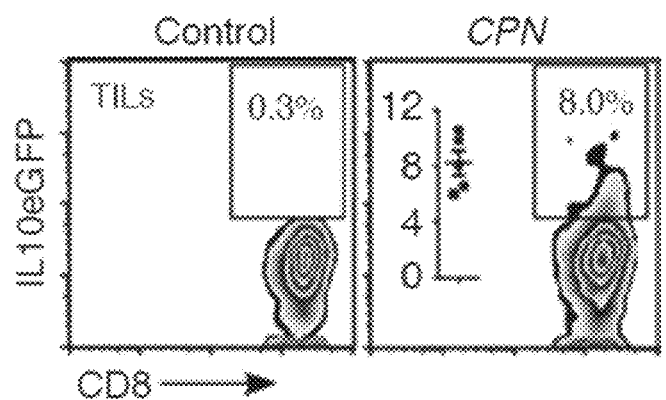
FIG. 6H shows the effect of carboxypeptidase N (CPN) expression in tumor cells on IL-10 production in CD8+ TILs. Control and CPN-expressing B16F10 cells ($4\times10^5$/mouse) were subcutaneously inoculated into WT Tiger mice. IL-10-reporter eGFP expression in CD8+ TILs was assayed at day 13. The right plot shows the percentages of IL-10+CD8+ TILs from 5 mice.
Figure 6I:
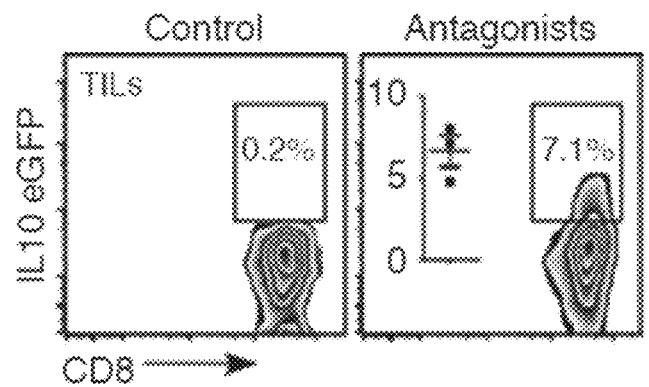
FIG. 6I shows the effect of C3aR and C5aR antagonists on IL-10 expression in CD8+ TILs. B16 tumor-bearing WT Tiger mice were treated with control or C3aR and C5aR antagonists (n=3 per group).
Figure 11E:
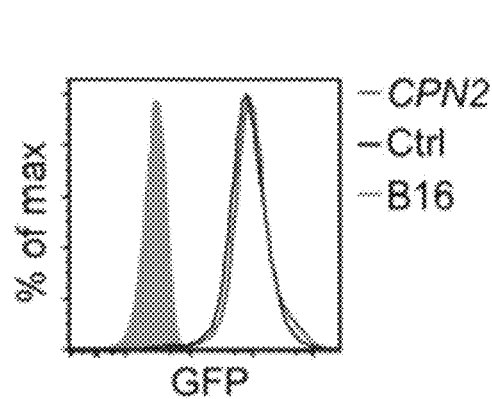
FIG. 11E shows flow cytometry analysis of CPN1-overexpressing B16 melanoma cells transduced with control GFP or CPN2-GFP virus. For FIGS. 11F-G, CD8+ T cells were activated by plate-bound anti-CD3/CD28 antibodies for 3 days. The expression of the complement receptors C3aR and C5aR was determined by flow cytometry at day 3 (FIG. 11F). The activated CD8+ T cells were then cultured in fresh medium without anti-CD3/CD28 antibodies for another 3 days. The expression of C3aR and C5aR was determined by flow cytometry (FIG. 11G). Results represent an average of three mice.

Anaphylatoxins, or complement peptides, are fragments that are produced as a result of activation of the complement system. Anaphylatoxins C3a and C5a were detected in freshly isolated B16 tumors from wild-type mice (FIG. 11C). To test the role of locally produced C3a and C5a in regulating IL-10 expression in CD8+ TILs, both subunits of carboxypeptidase N (CPN) 1 and 2 were overexpressed in B16 melanoma cells (FIG. 11D-E). Local overexpression of CPN inactivated anaphylatoxins (C3a and C5a) in the tumors from wild-type mice (FIG. 11C) and restored IL-10 production in CD8+ TILs to an extent similar to that in CD8+ TILs from tumors of C3−/− hosts (FIGS. 1E and 6H). In addition, blockade of C3aR and C5aR using antagonists also restored IL-10 production in vivo (FIG. 6I), indicating that locally produced C3a and C5a inhibit IL-10 production in CD8+ TILs.

Figure 6J:
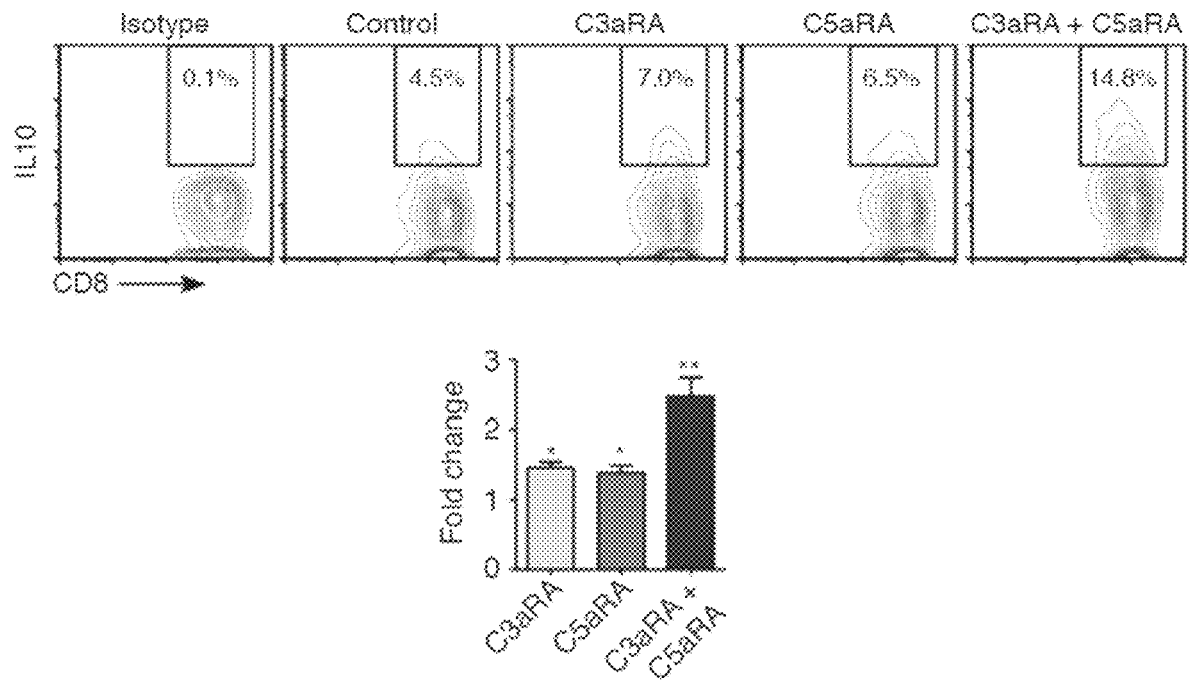
FIG. 6J shows the effect of C3aR and C5aR antagonists on IL-10 expression in in vitro-activated CD8+ T cells (n=4).
Figure 11F:
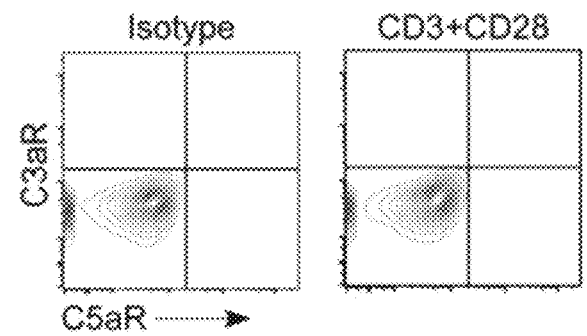
FIG. 11 shows that anaphylatoxins regulate IL-10 production through C3aR and C5aR.
FIG. 11A shows flow cytometry analysis of peritoneal macrophages harvested from a naïve mouse and stained with C3aR and isotype control antibodies.
FIG. 11B shows flow cytometry analysis of splenocytes collected from the spleen of a naïve mouse and stained with C5aR antibody.
FIG. 11C shows the levels of C3a and C5a in freshly isolated B16 tumors from wild type (WT), C3−/− mice, and CPN overexpressing B16 tumors from WT mice as well as ex vivo cultured B16 tumors from WT mice. C3a and C5a were quantified by ELISA. Culture medium was used as background (n=4 mice per group). For FIG. 11D, B16 melanoma cells were transduced with a control or CPN1 carrying virus and a CPN1-overexpressing stable line was selected with G418. The overexpression of CPN1 was confirmed by RT-PCR. β-actin was used as an internal control.
FIG. 11H shows the effect of complement signaling blockade on breast cancer development. E0771 breast cancer cells (1×10$^6$/mouse) were subcutaneously inoculated into WT mice. Mice were randomized into two groups and treated with C3aR antagonist or control solution every 12 hours starting from day 7 after tumor inoculation. Tumor volume was monitored every other day (n=6 mice per group). ns, p>0.05.
Figure 11G:
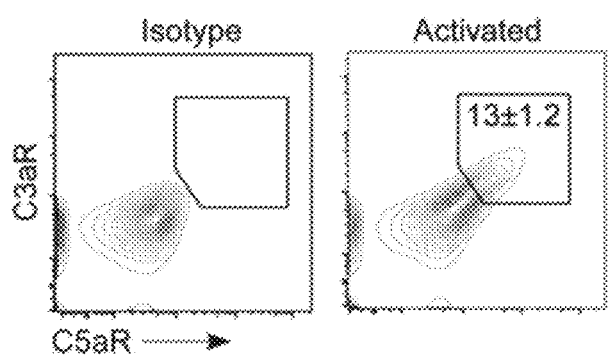

To determine whether anaphylatoxins inhibited IL-10 expression through C3aR and C5aR on CD8+ T cells, CD8+ T cells were purified and activated in vitro and C3aR and C5aR expression was determined. C3aR and C5aR were detected on activated CD8+ T cells only after long-term in vitro culture (FIG. 11F-G). C3aR or C5aR in vitro blockade alone using antagonist slightly increased IL-10 expression in activated CD8+ T cells, whereas combined blockade of both receptors further enhanced IL-10 expression in these cells (FIG. 6J). Taken together, the in vivo and in vitro results demonstrate that C3aR and C5aR have redundant suppressive functions in IL-10 production by CD8+ T cells.

Figure 6K:
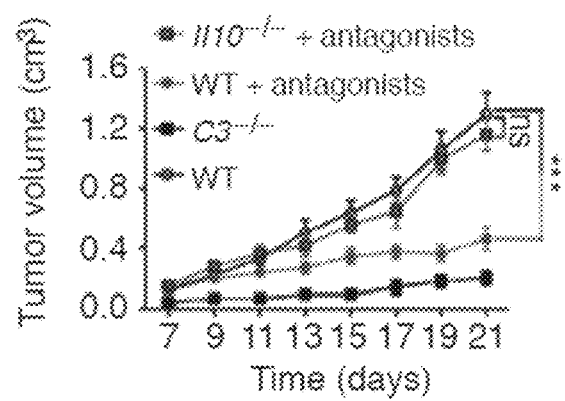
FIG. 6K shows the effect of complement signaling blockade on breast cancer development. E0771 breast cancer cells ($1\times10^6$/mouse) were subcutaneously inoculated into WT, C3−/−, and IL-10−/− mice. WT and IL-10−/−mice were treated with C3aR and C5aR antagonists or control solution every 12 hours starting from day 9 after tumor implantation. Tumor volume was monitored every other day (n=8 mice per group). For FIG. 6B and FIG. 6K, results are representative of three independent experiments. Bars and error bars indicate mean±SEM. Significance was determined by Student t test in B and by ANOVA in FIG. 6J and FIG. 6K(ns, P>0.05; *, P≤0.05; , P≤0.01; *, P≤0.001).
Figure 11H:
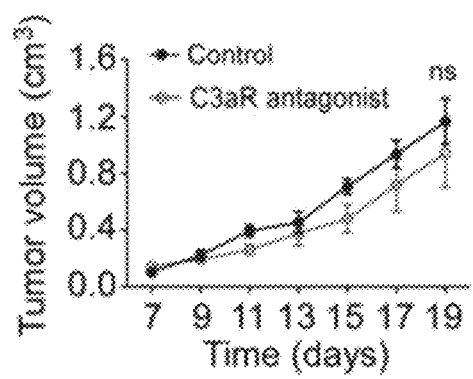

Whether blockade of the engagement of anaphylatoxins to their receptors could inhibit the development of established tumors was further investigated using complement receptor antagonists. SB 290157 is a nonpeptide small compound that was developed as a selective antagonist of C3aR. PMX205, the cyclic hexapeptide hydrocinnamate-(L-ornithine-proline-D-cyclohexylalanine-tryptophan-arginine), is a well-defined C5aR antagonist. Pharmacologic blockade of C3aR and C5aR by SB 290157 and PMX205 suppressed tumor growth in wild-type mice, and the efficacy was IL-10—dependent (FIG. 6K; FIG. 11H). These data demonstrate that C3aR and C5aR play important roles in complement-mediated suppression of IL-10 production and antitumor immunity. The results suggest that C3aR and C5aR expressed on CD8+ TILs may serve as novel immune checkpoint receptors that may be targeted for further immunotherapy of cancers.

Example 8

Complement Inhibits Antitumor Immunity through a PD-1-Independent Pathway

Figure 7A:
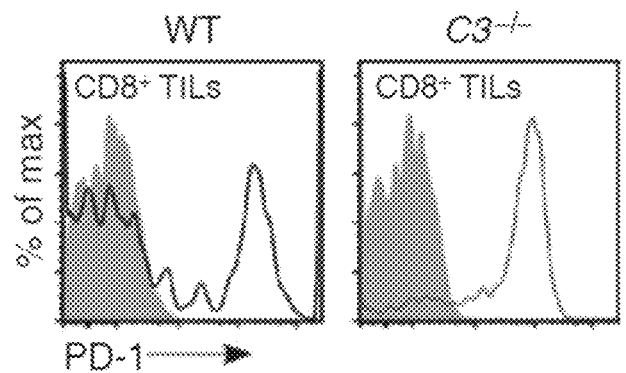
FIG. 7A shows expression levels of PD-1 on CD8+ TILs analyzed by flow cytometry at day 12 after tumor implantation.
Figure 7B:
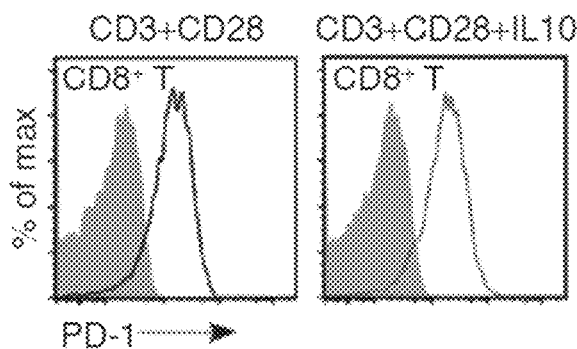
FIG. 7B shows the expression level of PD-1 on CD8+ T cells activated with anti-CD3/CD28 antibodies in the presence of IL-10. T cells from lymph nodes of naïve mice were activated by incubation with 3 μg/mL anti-CD3/CD28 antibodies for 48 hours with or without 500 U/mL IL-10 and analyzed for PD-1 expression.
Figure 7C:
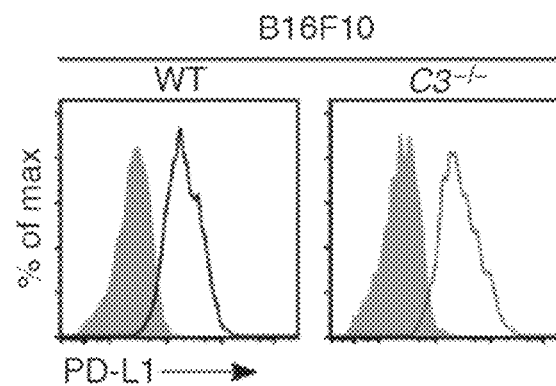
FIGS. 7C-D show PD-L1 expression on tumor cells developed in WT and C3−/− mice. B16F10 melanoma cells ($2\times10^5$/mouse) or E0771 breast cancer cells ($1\times10^6$/mouse) were subcutaneously inoculated into WT and C3−/− mice. PD-L1 expression in CD45-B16 tumor cells (FIG. 7C) and CD45-E0771 cells (FIG. 7D) was measured by flow cytometry at day 12 and day 19, respectively.
Figure 7D:
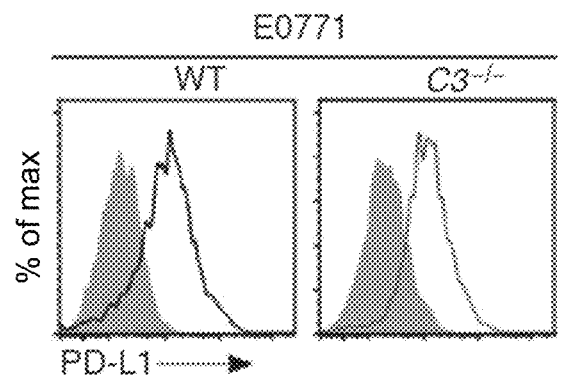
Figure 7E:
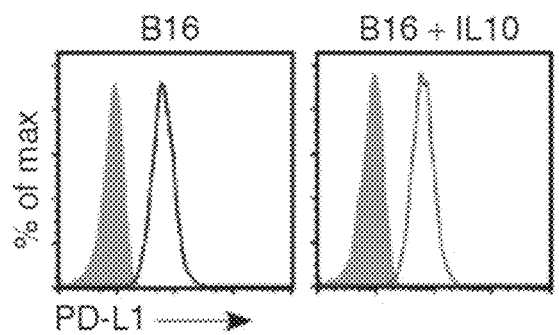
FIG. 7E shows PD-L1 expression in tumor cells after IL-10 stimulation. B16F10 cells were cultured with or without 500 U/mL IL-10 for 5 days. PD-L1 expression was analyzed by flow cytometry.

Immune checkpoint blockade with monoclonal antibodies targeting PD-1 expressed on CD8+ TILs results in an objective antitumor response in select patients. CD8+ TILs from C3−/− mice expressed comparable levels of PD-1 to those from wild-type mice (FIG. 7A). IL-10 did not modulate PD-1 expression on activated CD8+ T cells in vitro (FIG. 7B). Tumor cells from C3−/− mice expressed similar levels of PD-L1 compared with that from wild-type mice (FIGS. 7C and D). In addition, PD-L1 expression on tumor cells was not changed upon culture in IL-10-containing medium (FIG. 7E). These results demonstrate that IL-10 does not obviously regulate PD-1/PD-L1 expression in CD8+ T and tumor cells.

Figure 7F:
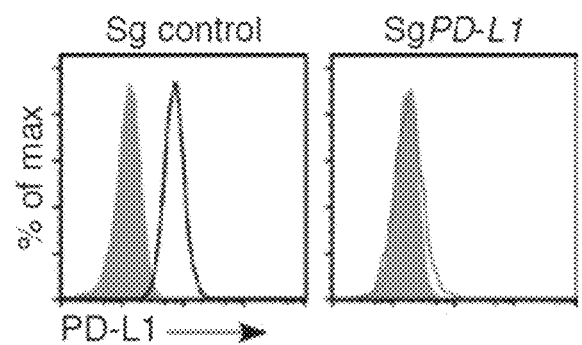
FIG. 7F shows PD-L1 expression on transduced B16F10 cells. B16F10 cells were transduced with control virus or single-guide RNA (sgRNA)—targeting PD-L1 virus and selected with puromycin to generate a stable PD-L1-silenced polyclonal cell line.
Figure 7G:
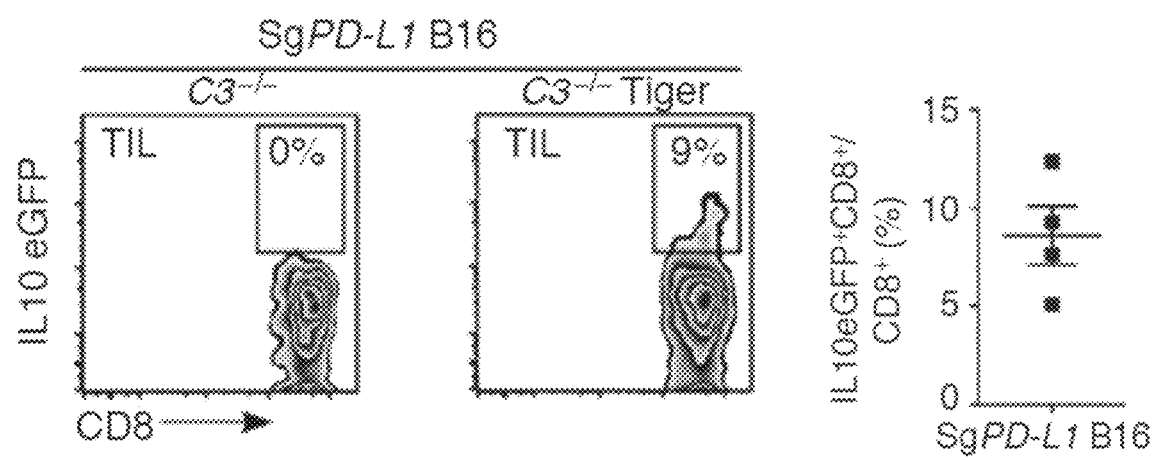
FIG. 7G shows IL-10 expression in CD8+ TILs from PD-L1-silenced B16F10 tumors. Control or PD-L1-silenced B16F10 melanoma cells ($4\times10^5$/mouse) were subcutaneously inoculated into C3−/− and C3−/− Tiger mice. GFP expression in CD3+CD8+ TILs was analyzed by flow cytometry. The right plot shows the percentages of IL-10+ CD8+ TILs from 4 individual mice.
Figure 7H:
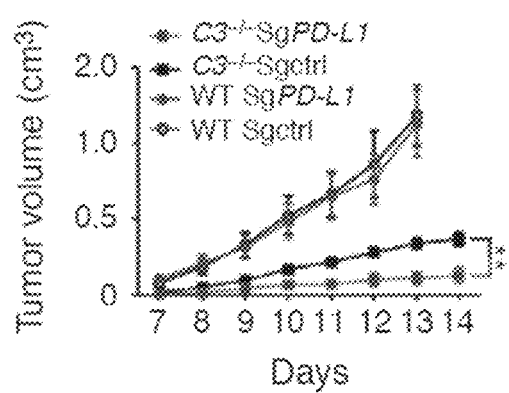
FIG. 7H shows the effect of blockade of PD-1/PD-L1 and complement signaling pathways on tumor development. Control or PD-L1-silenced B16F10 melanoma cells ($4\times10^5$/mouse) were subcutaneously inoculated into WT and C3−/− mice. Tumor development was monitored every day starting from day 7 after implantation (n=7, 7, 9, and 8 mice, respectively). For FIG. 7I, B16F10 melanoma cells ($5\times10^4$/mouse) were subcutaneously inoculated into WT mice. Mice were randomized into 4 groups 6 days after implantation. Each group of mice received control antibody, anti-PD-1 antibody, C3aR and C5aR antagonists, or anti-PD-1 antibody plus C3aR and C5aR antagonists (n=8 mice per group). For FIGS. 7A-F, solid gray color indicates isotype control staining. For FIGS. 7A-E, data represent a pool of 6 to 8 mice in each group. Significance was determined in FIG. 7H and FIG. 7I by Student t test.*, P≤0.05; **, P≤0.01.
Figure 7I:
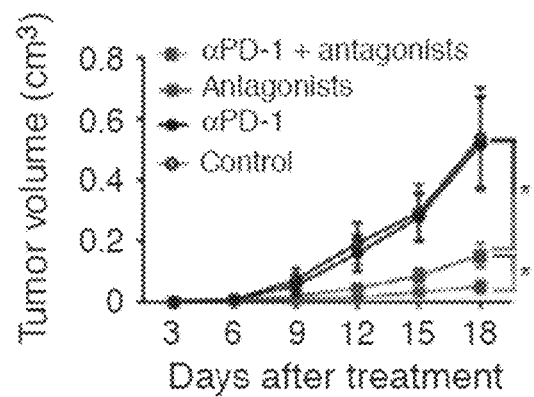
FIG. 7 shows that complement inhibits antitumor immunity through a PD-1-independent pathway. B16F10 melanoma cells ($2\times10^5$/mouse) were subcutaneously inoculated into wild-type (WT) and C3−/− mice.

A PD-L1-deficient B16 melanoma cell line was generated using CRISPR/Cas9-mediated gene editing (FIG. 7F). IL-10 expression in CD8+ TILs from PD-L1-deficient B16 tumors resembled that in CD8+ TILs from unmanipulated B16 tumors (FIGS. 1E and 7G), suggesting that PD-1 signaling does not regulate IL-10 production in CD8+ T cells in vivo. Based on these findings, the effect of combined blockade of complement signaling and PD-L1/PD-1 signaling pathways was tested. PD-L/—deficient tumors developed more slowly than the wild-type tumors in C3−/− mice (FIG. 7H). To further investigate the therapeutic effect of combined blockade of PD-1 and complement receptors on established tumors, B16 melanoma cells were implanted into a cohort of wild-type B6 mice. The tumor-bearing mice were randomized into four groups after 6 days of tumor development and treated with control antibody, anti-PD-1 blocking antibody, C3aR and C5aR antagonists, or a combination of anti-PD-1 blocking antibody with C3aR and C5aR antagonists. The anti-PD-1 blocking antibody alone did not show antitumor effects in the B16 melanoma model (FIG. 7I). However, combined treatment with anti-PD-1 blocking antibody plus C3aR and C5aR antagonists further enhanced the antitumor effect mediated by C3aR and C5aR blockade (FIG. 7I).

Example 9

Transcriptional Repression of IL-10 by Bach2

Figure 12A:
FIG. 12A shows the predicted Bach2 binding site in the IL-10 promoter.

To understand how complement signaling suppresses IL-10 expression in CD8+ TILs, published microarray data were searched to identify candidate genes with expression patterns similar or opposite to those in IL-10+-CD8+ T cells. The gene expression pattern of Bach2−/− T cells was similar to that of IL-10+CD8+ T cells. The IL-10 promoter sequence was retrieved from Transcriptional Regulatory Element database and the Bach2 binding site was predicted with a published algorithm using transfac positional weight matrices. The Bach2 binding site is shown in FIG. 12A.

Figure 12B:
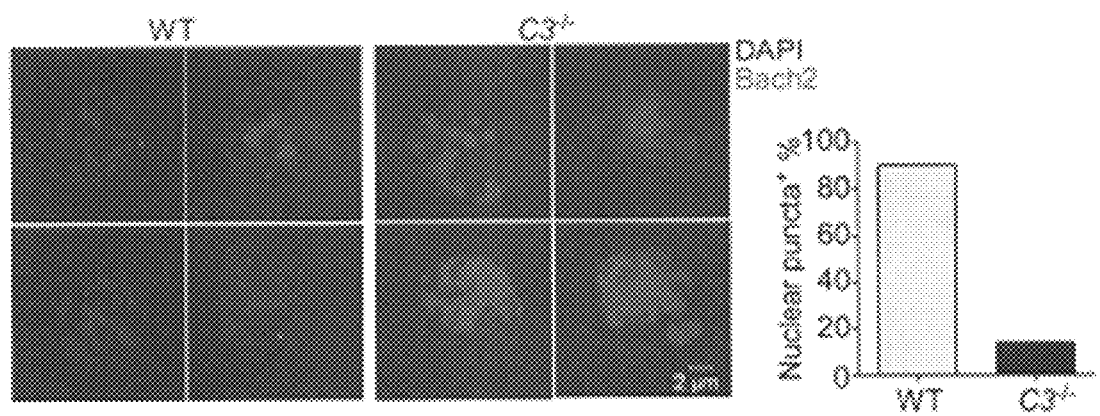
FIG. 12B shows confocal imaging of bach2 localization in C3aR+C5aR+CD8+ TILS from B16 melanoma developed in WT and C3−/− mice. Data represent a pool of 8-10 mice per group. Right panel shows the percentage of nuclear puncta in a total of 156 cells for WT and 192 cells for C3−/− mice.

Bach2 acts as both activator and repressor of transcription in CD4+ T cells to maintain their naive status. Confocal imaging analysis was conducted to determine the intracellular location of Bach2. Tumors were dissected and lymphocytes were enriched by Ficoll solution (GE lifesciences). After surface staining with anti-mouse Cd3, CD8, and C5aR, complement-positive CD8+ T cells were sorted by flow cytometry followed by a Bach2 and DAPI intracellular staining using True-Nuclear Transcription Factor Buffer Set (Biolegend). After cytopsin (Thermo Scientific), slides were mounted in Fluoromount-G (Southern Biotechnology). Sections were photographed using Zeiss 710 inverted confocal microscopy (Zeiss) and evaluated using imageJ software. As shown in FIG. 12B, Bach2 primarily localized as puncta in the nucleus of C3aR+C5aR+CD8+ TILS from wild-type mice, whereas Bach2 primarily localized in the cytoplasm in C3−/− mice.

Figure 12C:
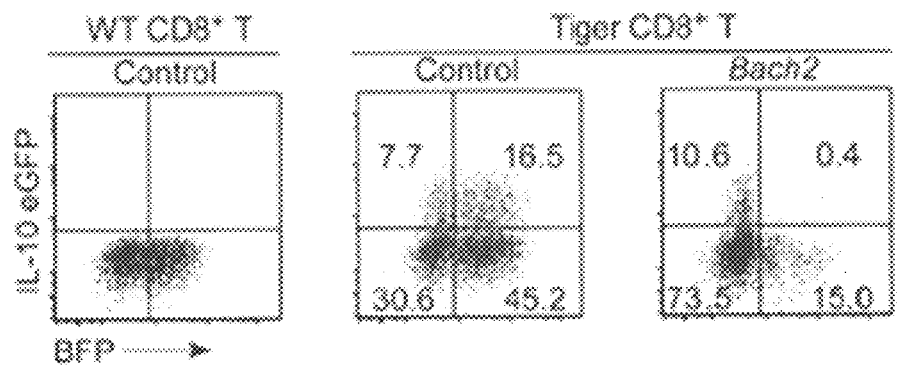
FIG. 12C shows the effect of Bach2 expression on IL-19 production in CD8+ T cells. T cells were activated by anti-CD3/CD28 antibodies for 24 hours, followed by control or Bach2 containing retrovirus transduction and then cultured with 100 u/ml IL-2 for 5-6 days. GFP expression was monitored by flow cytometry.
Figure 12D:
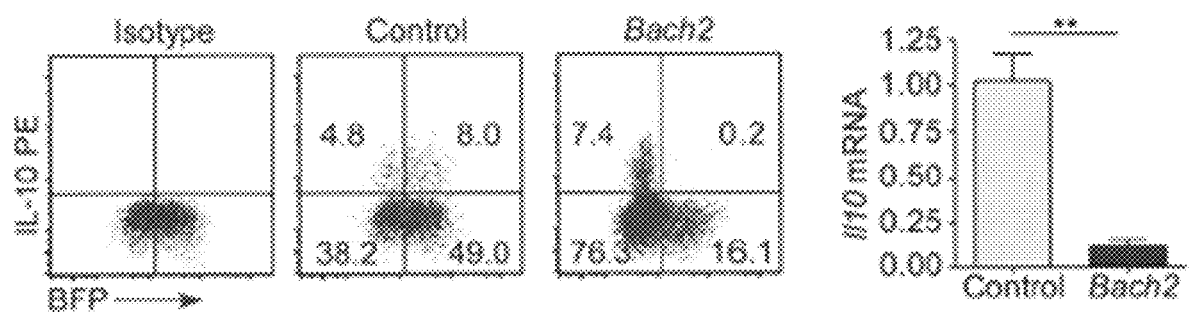
FIG. 12D shows intracellular staining for IL-10 in control and Bach2-expression CD8+ T cells as described in FIG. 12C. The infected T cells were stimulated with PMA and ionomycin for 4-6 hours before flow cytometry analysis.

To determine the effect of Bach2 expression on IL-10 production, Bach2 was overexpressed in activated primary CD8+ T cells from the IL-10 eGFP reporter mice. As shown in FIG. 12C, IL-10 production in Bach2-expressing CD8+ T cells was dramatically decreased. FIG. 12D shows intracellular staining for IL-10 in control and Bach2-expression CD8+ T cells as described in FIG. 12C. Bach2-expressing and control CD8+ T cells shown in FIG. 12D were sorted by flow cytometry and determined by real-time RT-PCR for IL-10 mRNA expression. RNA was isolated with Direct-Zol (Zymo Research) according to the manufacturer's protocol. Complementary DNA was synthesized with SuperScript III Reverse Transcriptase (Life Technologies). Quantitative real-time PCR was performed using a SYBR green-based assay (Applied Biosystems). For mRNA expression, 18s RNA was used for normalization across samples. Primers used were Mouse 18s rRNA (NOR_003278) forward: 5' TCGATGGTAGTCGCCGTGCCTA 3' (SEQ ID NO: 8), reverse: 5' GCCTGCTGCCTTCCTTGGATGT 3' (SEQ ID NO: 9); Mouse IL-10 (NM 010548) forward: 5' AGCCGG-GAAGACAATAACTG 3' (SEQ ID NO: 10), reverse: 5' GGAGTCGGTTAGCAGTATGTTG 3' (SEQ ID NO: 11); Mouse CPN1 (NM030703) forward: 5' GGTGGACCT-GAACCGCAACT TC 3' (SEQ ID NO: 12), reverse: 5' CGTTGGTGATGCCGTCTGGAA 3' (SEQ ID NO: 5); reverse; 5' CGTTGGTGATGCCGTCTGGAA 3' (SEQ ID NO: 13); Mouse β-Actin (NM_007397) forward: 5' ACCTTCTACAATGAGCTGCG 3' (SEQ ID NO: 15), reverse: 5' CTGGATGGCTACGTACATGG 3' (SEQ ID NO: 16).

Figure 13:
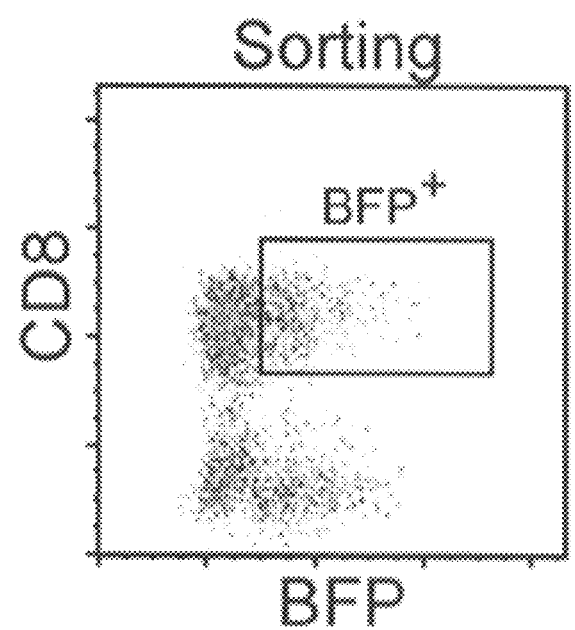
FIG. 13 shows mRNA expression in Bach2 overexpressing CD8+ T cells. T cells were activated by anti-CD3/CD28 antibodies for 24 hours, followed by control or Bach2 containing retrovirus transduction and then cultured with 100 U/ml IL-2 for 5-6 days. BFP positive CD8+ T cells were sorted by flow cytometry and RNA was extracted for real-time PCR assay.

FIG. 12E and FIG. 13 show decreased Il10 mRNA level in Bach2-expressing CD8+ T cells. Taken together, these data suggest that complement signaling promotes the nuclear localization of Bach2, where suppresses Il10 transcription in CD8+ TILs.

Example 10 hIL-10 anti-human PD-1 Fusion Protein

The V region coding region of anti-PD-1 monoclonal antibody was synthesized. The V region of heavy chain and light chain were cloned into AbVec immunoglobulin G1 and AbVec-k, respectively. Next, human Il-10 coding region was inserted into the C terminal of the heavy chain as a fusion protein with an SGGGGSGGGGSGGGGSGGGG (SEQ ID NO: 17) linker. The whole heavy chain with human IL-10 and the light chain were cloned to pEE6.4 and pEE12.4 (Lonza), respectively. Next, both vectors were digested by Not1 and BamH1 restriction enzymes. The complete human cytomegalovirus major immediate-early heavy chain/simian virus 40 transcription unit form-digested pEE6.4 plasmid was ligated into the large Not1-BamH1 fragment from the digested pEE12.4 plasmid containing the light-chain expression cassette. The plasmid containing both heavy and light chains was transfected into Chinese hamster ovary cells, and stable clones were established for the production of IL-10/antiPD-1 fusion.

The function of the anti-PD-1-IL-10 fusion protein may be examined in vivo using E0771 and 4T1 breast cancer models in comparison with anti-PD-1 alone as well as anti-PD-1 plus co-administration of free IL-10. The effect of these treatments on TIL cell population and tumor growth may be analyzed.

Example 11

IL-10/PD-1 Fusion Proteins

Because both IL-10 and anti-PD-1 target CD8+ TILs and have very different modes of action, it is expected that a targeted interleukin-10 molecule comprising an IL-10 moiety joined with a targeting moiety comprising an anti-PD-1 antibody as a fusion protein will effectively target CD8+ TILs with high efficacy and while minimizing its inhibitory effects on a wide array of other cell populations. CD8+ TILs expressing high levels of PD-1 (PD-1$^{high}$ cells) are highly enriched for antitumor activity. Thus, an anti-PD-1-IL-10 fusion will be prepared to deliver IL-10 to PD-1$^{high}$ CD8+ TILs and test its antitumor activity.

The polypeptide sequences derived from a fully human anti-human PD-1 mAb that also blocks mouse PD-1 by Medarex Inc. (as described in U.S. Pat. No. 8,008,449 B2, which is hereby incorporated by reference in its entirety) will be used. The V region of the heavy chain and light chain of anti-human PD-1 will be cloned into AbVec immunoglobulin G1 and AbVec-κ, respectively. Mouse IL-10 coding region will be inserted into the C terminal of heavy chain as a fusion protein with a linker. The whole heavy chain fused with IL-10 and the light chain will be cloned to pEE6.4 and pEE12.4 (Lonza), respectively, and then the two plasmids will be re-ligated. The plasmid containing both heavy and light chains will be transfected into CHO cells to generate anti-PD-1-IL-10 fusion proteins.

The function of anti-PD-1-IL-10 will be evaluated in vitro to ensure it functions properly. The efficacy of anti-PD-1-IL-10 will be evaluated in vivo using E0771 and 4T1 breast cancer models in comparison with anti-PD-1 alone as well as anti-PD-1 plus co-administration of free IL-10. The effect of these treatments on TIL cell population will be analyzed. Because PD-1 is also expressed by other cell types, such as B cells, myeloid dendritic cells, and monocytes, the overall antitumor effect of the anti-PD-1-IL-10 fusion protein may derive from its impact on all these cell types. Thus, the overall effect of the anti-PD-1-IL-10 fusion protein will also be tested in vivo. Other targeted interleukin-10 molecules, such as anti-TIM3-IL-10 fusion protein or anti-LAG3-IL-10 fusion protein, may also be tested as described.

Example 12

Ex Vivo Conditioning with IL-10

Peripheral pmel-1 CD8+ T cells from spleen and lymph nodes of TCR transgenic mice will be activated with anti-CD3/CD28, expanded ex vivo with IL-2 or IL-2 plus IL-10, and transferred into cyclophosphamide-treated lymphopenic C57BL/6 mice with or without B16 melanoma tumors (CD45.2). In wild type B6 mice without tumor, the homeostasis of the transferred IL-10-conditioned pmel-1 CD8+ T cells in lymphodepleted host will be examined, including the number, location, persistence, functional phenotype (IFNγ, TNFα, perforin, and granzyme B expression) and their capability to form different memory cell populations (TCM, TEM) 2-24 weeks after the adoptive transfer.

In wild type B6 mice bearing B16 melanoma, the homeostasis and the antitumor efficacy of the transferred IL-10-conditioned pmel-1 CD8+ T cells will be examined. In addition, the molecular and functional phenotype of the IL-10-conditioned pmel-1 CD8+ TILs will be characterized in the tumors. To further mimic a clinical setting, pmel-1 TCR α and β gene will be retrovirally transduced into CD8+ T cells from non-transgenic wild type C57BL/6 mice after activation and tested the same way as described above.

Example 13

Ex Vivo Conditioning

The effect of ex vivo conditioning with C3aR/C5aR1 antagonists on antitumor mouse CD8+ T cell function in vivo will be evaluated. Treatment of CD8+ T cells with C3aR/C5aR1 antagonists results in IL-10 production, but it will be tested whether C3aR/C5aR1 antagonists promote antitumor immunity primarily through induction of IL-10 as IL-10 is required for their antitumor efficacy. The ex vivo conditioning of antitumor CD8+ T cells with C3aR/C5aR1 antagonists and will be tested. The peripheral pmel-1 CD8+ T cells from either transgenic mice or retroviral transduction will be expanded with IL-2 or IL-2 plus C3aR/C5aR1 antagonists and tested as described in Example 11. These experiments will determine whether ex vivo conditioning of peripheral antigen-specific T cells with IL-10 or C3aR/C5aR1 antagonists results in potent antitumor efficacy and long lasting tumor-specific CD8+ memory T cells when transferred into lymphodepleted hosts and whether these two conditioning techniques have similar in vivo effect. As C3aR/C5aR1 signaling inhibits IL-12 production in macrophages, conditioning of T cells with C3aR/C5aR1 antagonists may lead to production of both IL-10 and IL-12 and potent CTLs.

Next, the effect of in vivo conditioning with IL-10 on antitumor mouse CD8+ T cell function will be tested. In vivo conditioning of antitumor CD8+ T cells by constitutively expressing IL-2 or IL-12 through retroviral transduction has not been clinically applied. Pegylated IL-10 has a manageable adverse effect profile in cancer patients, suggesting that in vivo IL-10 expression in CD8+ T cells is feasible. Experiments will be performed to activate pmel-1 CD8+ T cells with anti-CD3/CD28 and transduce the activated CD8+ T cells using anMSCV-based IL-10-GFP-expressing retroviral vector. The IL-10 expression level will be analyzed in viral transduced T cells. GFP+IL-10 expressing pmel-1 CD8+ T cells will be sorted at 3-5×10$^6$/mouse and adoptively transferred into lymphodepleted wild type B6 mice with or without B16 melanoma tumors (CD45.2). The homeostasis and antitumor capability of the transferred IL-10 expressing pmel-1 CD8+ T cells will be analyzed as in Example 11.

The effect of ex vivo and in vivo conditioning with IL-10 and C3aR/C5aR1 antagonists on human TCR-engineered T cells will be assessed. To facilitate translation into clinical application, the effect of IL-10 and C3aR/C5aR1 antagonists on the homeostasis of human TIL 13831 TCR-engineered T cells in vivo will be tested. TIL 13831 TCR (as described by Roszkowski et al., Cancer Res. 65(4):1570-6 (2005) recognizes an HLA-A2-restricted tyrosinase368-376, a highly expressed antigen in melanoma tumors. A direct comparison will be made on the conditioning efficacy among IL-10, C3aR/C5aR1 antagonists and IL-12 using an in vivo model. Human PBMCs will be stimulated with anti-CD3 (OKT3) and cultured for 3 days with IL-2, and transfected with the antitumor TIL 13831 TCRα and β chain gene. On day 8 when cells are in the rapid expansion protocol (REP) phase, IL-10, C3aR/C5aR1 antagonists, or IL-12 will be added into the culture continuously for 3 weeks. At the end of the in vitro culture, the number and functional status of TIL 13831 TCR CD8+ T cells will be determined. Furthermore, these expanded TIL 13831 TCR-gene engineered human T cells will be transferred into immunodeficient NOD-scid/IL-2Rγnull (NSG mice, the Jackson Lab, 005557). The number, location, persistence, and functional status of the TCR gene-engineered human T cells will be determined 1-5 weeks after the transfer.

Example 14

Human TIL Expansion

The effect of C3aR/C5aR1 antagonists on human TIL expansion will be tested. TILs from NSCLC and TNBC patients will be isolated and cultured in the presence of IL-2 or IL-2 plus C3aR/C5aR1 antagonists. The number, antitumor CTL activity, and effector molecule production will be measured in vitro. In addition, the effect of IL-10 and C3aR/C5aR1 antagonists conditioning on in vivo homeostasis of human TILs will be tested. Human TILs from NSCLC and TNBC will be isolated and cultured in the presence of IL-2 or IL-2 plus C3aR/C5aR1 antagonists, and then injected into NSG mice. The number, persistence, location, and functional status of the human TILs 1-5 weeks after the transfer will be determined. These experiments will determine whether IL-10 and C3aR/C5aR1 antagonists promote the generation of large number of potent antitumor human TILs to treat lung and breast cancer.

The above experiments will address how to better utilize IL-10 and C3aR/C5aR antagonists in immune checkpoint blockade- and ACT based immunotherapies. It is anticipated that a rational use of IL-10, alone or in combination, will enhance current immunotherapies. Given the plural roles of complement signaling (inhibiting IL-10 production in CD8+ TILs and NK cell activation, promoting MDSC recruitment to the TME) in suppressing host antitumor immunity, complement signaling inhibitor-based cancer immunotherapy will likely open a new avenue for clinical application.

6. Clauses

For reasons of completeness, various aspects of the present disclosure are set out in the following numbered clauses:

Clause 1: A method for treating a cancer in a subject in need thereof, the method comprising: isolating CD8+ T cells from a sample derived from a subject, exposing the CD8+ T cells to interleukin-10, exposing the CD8+ T cells to interleukin-2, expanding the CD8+ T cells, and administering the expanded CD8+ T cells to the subject.

Clause 2: The method of clause 1, wherein the CD8+ T cells are exposed to interleukin-2 prior to being exposed to interleukin-10.

Clause 3: The method of clause 1, wherein the CD8+ T cells are exposed to interleukin-2 and interleukin-10 simultaneously.

Clause 4: The method of clause 1, wherein the CD8+ T cells are exposed to interleukin-2 and interleukin-10 for about 1 hour to about 24 hours.

Clause 5: The method of clause 1, wherein the CD8+ T cells are expanded to at least $10^6$ CD8+ T cells prior to administration to the subject.

Clause 6: The method of clause 1, further comprising administering to the subject a therapeutically effective amount of a complement inhibitor.

Clause 7: The method of clause 1, further comprising exposing the isolated CD8+ T cells to a complement inhibitor prior to administering the CD8+ T cells to the subject.

Clause 8: The method of any one of clauses 6 or 7, wherein the complement inhibitor comprises one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof.

Clause 9: The method any one of clauses 1-8, further comprising administering to the subject at least one of cisplatin, oxaliplatin, a kinase inhibitor, trastuzumab, cetuximab, panitumumab, lambrolizumab and nivolumab.

Clause 10: The method of any one of clauses 1-9, wherein the cancer is selected from the group consisting of head cancer, neck cancer, B-cell non-Hodgkin's lymphoma, chronic lymphocytic leukemia, multiple myeloma, colorectal cancer, non-small cell lung cancer, solid tumors (including advanced solid tumors), breast cancer, melanoma, prostate cancer, renal cell carcinoma, diffuse large cell lymphoma, advanced CD70+ cancers, CD20+ non-Hodgkin's lymphoma, and a hematologic malignancy.

Clause 11: The method of clause 1, wherein the sample is a blood sample.

Clause 12: The method of clause 1, wherein the sample is a tissue sample.

Clause 13: The method of clause 1, wherein the sample is a tumor sample.

What is claimed is:

1. A method for treating a cancer in a subject in need thereof, the method comprising:
   (a) isolating CD8+ tumor infiltrated T lymphocyte (TIL) cells from a solid tumor sample derived from a subject;
   (b) exposing the CD8+ TIL cells to interleukin-2 and interleukin-10;
   (c) expanding the CD8+ TIL cells;
   (d) further exposing the expanded CD8+ TIL cells to one or more of C5aR complement inhibitor or C3aR complement inhibitor to induce interleukin-10 expression in the expanded CD8+ TIL cells; and
   (e) administering the CD8+ TIL cells of step (d) to the subject.

2. The method of claim 1, wherein the CD8+ TIL cells are exposed to interleukin-2 prior to being exposed to interleukin-10.

3. The method of claim 1, wherein the CD8+ TIL cells are exposed to interleukin-2 and interleukin-10 simultaneously.

4. The method of claim 1, wherein the CD8+ TIL cells are exposed to interleukin-2 and interleukin-10 for about 1 hour to about 24 hours.

5. The method of claim 1, wherein the CD8+ TIL cells are expanded to at least $10^6$ CD8+ TIL cells prior to administration to the subject.

6. The method of claim 1, further comprising administering to the subject a therapeutically effective amount of a complement inhibitor.

7. The method of claim 6, wherein the complement inhibitor comprises one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof.

8. The method of claim 1, further comprising administering to the subject at least one of cisplatin, oxaliplatin, a kinase inhibitor, trastuzumab, cetuximab, panitumumab, lambrolizumab and nivolumab.

9. The method of claim 1, wherein the cancer is selected from the group consisting of head cancer, neck cancer, B-cell non-Hodgkin's lymphoma, chronic lymphocytic leukemia, multiple myeloma, colorectal cancer, non-small cell lung cancer, solid tumors (including advanced solid tumors), breast cancer, melanoma, prostate cancer, renal cell carcinoma, diffuse large cell lymphoma, advanced CD70+ cancers, CD20+ non-Hodgkin's lymphoma, and a hematologic malignancy.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
agcctgctgt cacttgctac        20

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
caccgagcct gctgtcactt gctac                                              25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
aaacgtagca agtgacagca ggctc                                              25

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ggtggacctg aaccgcaact tc                                                 22

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
cgttggtgat gccgtctgga a                                                  21

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
accttctaca atgagctgcg                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ctggatggct acgtacatgg                                                    20

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tcgatggtag tcgccgtgcc ta                                            22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gcctgctgcc ttccttggat gt                                            22

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
agccgggaag acaataactg                                               20

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ggagtcggtt agcagtatgt tg                                            22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
ggtggacctg aaccgcaact tc                                            22

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
cgttggtgat gccgtctgga a                                             21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
cgttggtgat gccgtctgga a                                             21

<210> SEQ ID NO 15

```
<211> LENGTH: 20
<212> TYPE: DNA
<213> ORGANISM: Artificial Sequence
<220> FEATURE:
<223> OTHER INFORMATION: Synthetic

<400> SEQUENCE: 15
accttctaca atgagctgcg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ctggatggct acgtacatgg                                               20

<210> SEQ ID NO 17
<211> LENGTH: 20
<212> TYPE: PRT
<213> ORGANISM: Homo sapiens

<400> SEQUENCE: 17

Ser Gly Gly Gly Gly Ser Gly Gly Gly Ser Gly Gly Gly Gly Ser
1               5                   10                  15
Gly Gly Gly Gly
            20

<210> SEQ ID NO 18
<211> LENGTH: 33
<212> TYPE: DNA
<213> ORGANISM: Mus musculus

<400> SEQUENCE: 18
ggtgacttcc gagtcagcaa gaaatatcgg acg                                33

<210> SEQ ID NO 19
<211> LENGTH: 36
<212> TYPE: DNA
<213> ORGANISM: Artificial Sequence
<220> FEATURE:
<223> OTHER INFORMATION: Synthetic

<400> SEQUENCE: 19
ggtgacttcc gagtcagcaa gaaatatcgg acgatg                             36

<210> SEQ ID NO 20
<211> LENGTH: 36
<212> TYPE: DNA
<213> ORGANISM: Artificial Sequence
<220> FEATURE:
<223> OTHER INFORMATION: Synthetic

<400> SEQUENCE: 20
ccactgaagg ctcagtcgtt ctttatagcc tgctac                             36
```